US007553821B2

(12) United States Patent
Altieri

(10) Patent No.: US 7,553,821 B2
(45) Date of Patent: Jun. 30, 2009

(54) METHODS FOR SELECTIVELY MODULATING SURVIVIN APOPTOSIS PATHWAYS

(75) Inventor: Dario C. Altieri, Hamden, CT (US)

(73) Assignee: Yale University, New Haven, CT (US)

( * ) Notice: Subject to any disclaimer, the term of this patent is extended or adjusted under 35 U.S.C. 154(b) by 437 days.

(21) Appl. No.: 10/291,607

(22) Filed: Nov. 12, 2002

(65) Prior Publication Data

US 2003/0143232 A1 Jul. 31, 2003

Related U.S. Application Data

(62) Division of application No. 09/515,514, filed on Feb. 29, 2000, now Pat. No. 6,509,162.

(51) Int. Cl.
*A61K 48/00* (2006.01)
(52) U.S. Cl. ...................................................... 514/44
(58) Field of Classification Search ........................ None
See application file for complete search history.

(56) References Cited

U.S. PATENT DOCUMENTS

| 6,028,171 | A | 2/2000 | Olsson et al. ............... 530/328 |
| 6,077,709 | A * | 6/2000 | Bennett et al. .............. 435/375 |
| 6,335,194 | B1 * | 1/2002 | Bennett et al. .............. 435/375 |

FOREIGN PATENT DOCUMENTS

| WO | WO 95/20655 | 8/1995 |
| WO | WO 98/22589 | 5/1998 |

OTHER PUBLICATIONS

Ambrosini et al., J. Biol. Chem., vol. 273, pp. 11177-11182.*
Adida et al., "Developmentally Regulated Expression of the Novel Cancer Anti-Apoptosis Gene *Survivin* in Human and Mouse Differentiation," *A J Pathol*, 152(1):43-49, 1998.
Altieri, "Xa receptor EPR-1", *FASEB J* 9:860-865, 1995.
Ambrosini et al., "A Novel Anti-Apoptosis Gene, *Survivin*, Expressed in Cancer and Lymphoma," *Nature Med*, 3(8):917-921, 1997.
Ambrosini et al., "Molecular Dissection of Effector Cell Protease Receptor-1 Recognition of Factor Xa", *The Journal of Biological Chemistry*, vol. 271, (2) 1243-1248, 1996.
Birnbaum, M.J. et al., "An Apoptosis-Inhibiting Gene from a Nuclear Polyhedrosis Virus Encoding a Polypeptide with CYS/HIS Sequence Motifs", *J Virology* 68:2521-2528, 1994.
Clem, R.J. et al., "Control of Programmed Cell Death by the Baculovirus Gene *p35* and *iap* ", Mol Cell Biol 14:5212-5222, 1994.
Clem et al., "Anti-Apoptosis Genes of Baculoviruses," *Cell Death and Differentiation*, 3(1):9-16, 1996.
Ding et al., "The Spindle Pole Body of *Schizosaccharomyces pombe* Enters and Leaves the Nuclear Envelope as the Cell Cycle Proceeds ," *Mol Biol Cell*, 8(8):1461-1479, 1997.
Duchosal, et al., "In vivo Immunosuppression by Targeting a Novel Protease Receptor", *Nature*, vol. 380: 352-356, 1996.
Duckett, C.S. et al., "A Conserved Family of Cellular Genes Related to the Baculovirus IAP Gene and Encoding Apoptosis Inhibitors", *EMBO J* 15:2685-2694, 1996.
Gordon et al., "New Gene Product Prevents Apoptosis in Colon, Pancreas Cancers ," *Gastroenterology*, 113(4):1060, 1997.
Grossman et al., Expression of the Apoptosis Inhibitor, Survivin, In Nonmelanoma Skin Cancer and Gene Targeting in a Keratinocyte Cell Line, *Lab Invest.*, 79, 1121, 1999.
Grossman, et al., "Expression and targeting of the apoptosis inhibitor, survivin, in human melanoma", *J. Invest.* Dermatol., 113, 1076-81, 1999.
Hay, B.A. et al., "Drosophila Homologs of Baculovirus Inhibitor of Apoptosis Proteins Function to Block Cell Death", *Cell* 83:1253-1262, 1995.
Horio et al., "Human γ- Functions in Fission Yeast," *J Cell Biol*, 126(6):1465-1473, 1994.
Ibrado et al., "BCI-$x_L$ Overexpression Inhibits Taxol-induced Yama Protease Activity and Apoptosis," *Cell Growth Diff*, 7(8):1087-1094, 1996.
Lajoie-Mazenc et al., "Recruitment of Antigenic gamma-Tubulin during Mitosis in Animal Cells: Presence of gamma-Tubulin in the Mitotoic Spindle ," *J Cell Sci*, 107(10):2825-2837, 1994.
Li et al., "Pleiotropic Cell-division Defects and Apoptosis Induced by Interference with Survivin Function" *Nat. Cell Biolog.*, 1, 461-466, 1999.
Liston, P. et al., "Suppression of Apoptosis in Mammalian Cells by NAIP and a Related Family of IAP Genes", *Nature*, 379:349-353, 1996.
Martin et al., "The Role of γ- Tubulin in Mitotic Spindle Formation and Cell Cycle Progression in *Aspergillus nidulans*," *J Cell Sci*, 110(5):623-633, 1997.
Minn et al., "Expression of Bcl-$x_L$ and Loss of p53 Can Cooperate to Overcome a Cell Cycle Checkpoint Induced by Mitotic Spindle Damage," *Genes & Dev* , 10(2):2621-2631, 1996.
Morgan et al., "p53 and ATM: Cell Cycle, Cell Death, and Cancer," *Adv Can Res*, 71:1-25, 1997.
Nurse, P., "Ordering S phase and M phase in the cell cycle", *Cell*, 79:547-550, 1994.
Rothe, M. et al., "The TNFR2-TRAF Signaling Complex Contains Two Novel Proteins Related to Baculoviral Inhibitor of Apoptosis Proteins", *Cell*, 83:1243-1252. 1995.
Roy, N. et al., "The Gene for Neuronal Apoptosis Inhibitory Protein Is Partially Deleted in Individuals with Spinal Muscular Atrophy," *Cell*, 80:167-178, 1995.
Sorger et al., "Coupling Cell Division and Cell Death to Microtubule Dynamics," *Curr Opin Cell Biol*, 9(6):807-814, 1997.
Willingham et al., Transient Mitotic Phase Localization and Bci-2 Oncoprotein in Human Carcinoma Cells and Its Possible Role in Prevention of Apoptosis, J Histochem Cytochem, 42(4):441-450, 1994.

(Continued)

*Primary Examiner*—Misook Yu
(74) *Attorney, Agent, or Firm*—Morgan, Lewis & Bockius LLP

(57) ABSTRACT

The present invention, based on the discovery of a new biological phenomena, provides methods and compositions for use in identifying agents that modulate the phosphorylation of survivin, the interaction between survivin and p34$^{cdc2}$-cyclin B1 kinase complex, and the interaction between survivin and caspase-9. Related methods and compositions can be used to modulate survivin regulated apoptosis.

7 Claims, 18 Drawing Sheets

OTHER PUBLICATIONS

M. Hengarther, "*Cell Death and Aging, In Molecular Mechanisms in Molecular Biology and Biotechnology*," pp. 158-162, *ed*. R.A. Meyers, VCH Publishers, NY, NY 1995.

Zou et al., "An APAF-1-cytochrome c multimeric complex is a functional apoptosome that activates procaspase-9" *J. Biol. Chem.*, 274: 11549-11556, 1999.

Borgne and Meijer, "Sequential dephosphorylation of p34$^{cdc2}$ on Thr-14 and Tyr-15 at the prophase/metaphase transition," *J Biol Chem*, 271(44):27847-27854, 1996.

Li et al., "Control of apoptosis and mitotic spindle checkpoint by survivin," *Nature*, 396(6711): 580-584, 1998.

O'Connor et al., "Regualtion of apoptosis at cell division by p34$^{cdc2}$ phosphorylation of survivin," *Proc Natl Acad Sci U. S. A.*, 97(24):13103-13107, 2000.

Trzepaca et al., "Phosphorylation of the tumor suppressor *Adenomatous polyposis coli* (APC) by the cyclin-dependent kinase p34$^{cdc2}$," *J Biol Chem*, 272(35): 21681-21684, 1997.

Holmes, et al., 1996, J Biol. Chem., vol. 271, No. 4, pp. 25240-25246.

Kendrew, Sir John; *Journal of Molecular Biology*,1994, pp. 113.

* cited by examiner

FIG. 1A
p34$^{cdc2}$ consensus site:    S/TPXK/R
| | | |
|---|---|---|
| Survivin (Human) | 31 | CACTPERMA |
| Survivin (Mouse) | 31 | CACTPERMA |
| BRUCE (Human) | 277 | RWAQPDPMA |
| NAIP (Human) | 76 | .WI.PQEMA |
| XIAP (Human) | 42 | .PVSASTLA |
| BIR1 (C.elegans) | 35 | AKCSQAVAA |
| BIRP (S.Pombe) | 37 | AKPTPETLA |
| BIR-1 (S.Cerv.) | 40 | KVIPYQAMA |
| OpIAP (Baculovirus) | 32 | FQLEPSRMA |
| DIAP (Drosophila) | 58 | WDLDKRQLA |
FIG. 1B
Kinase: p34$^{cdc2}$-cyclin B1
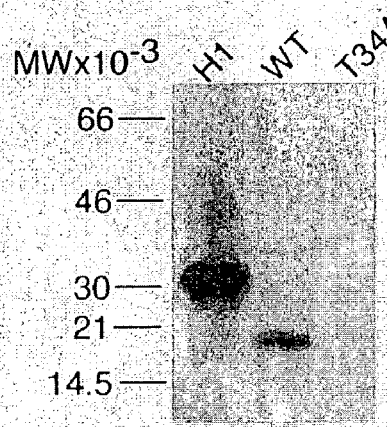
Kinase: Cdk2-cyclin E
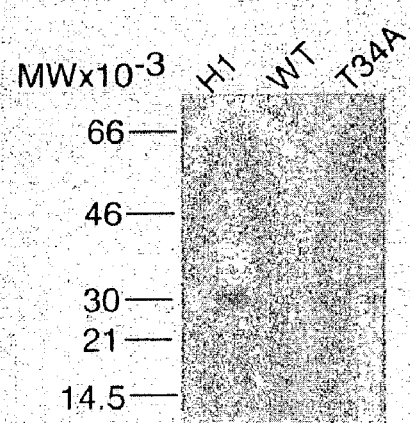

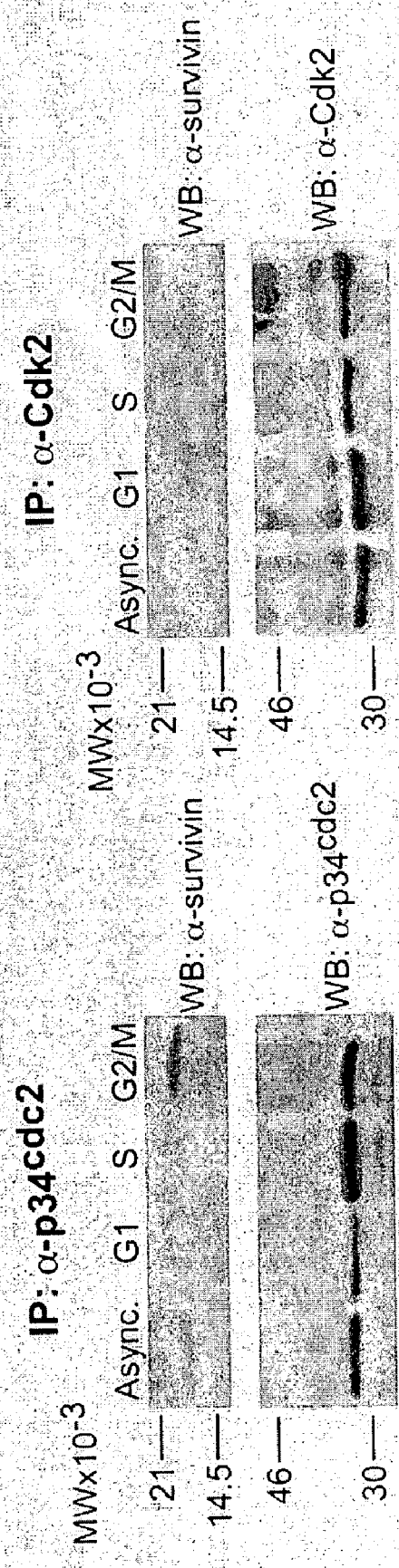

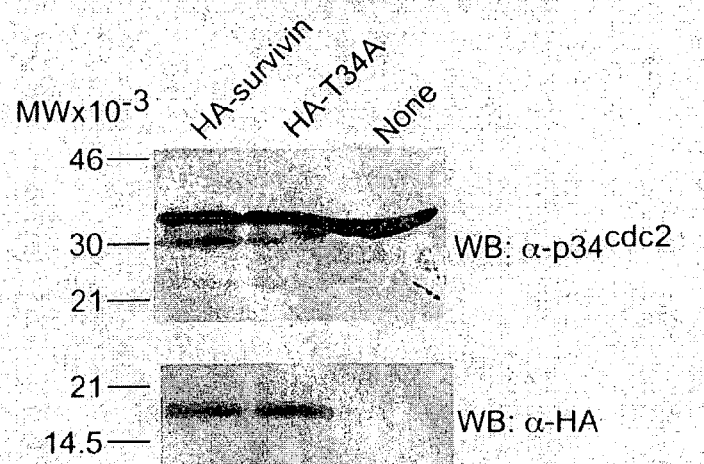
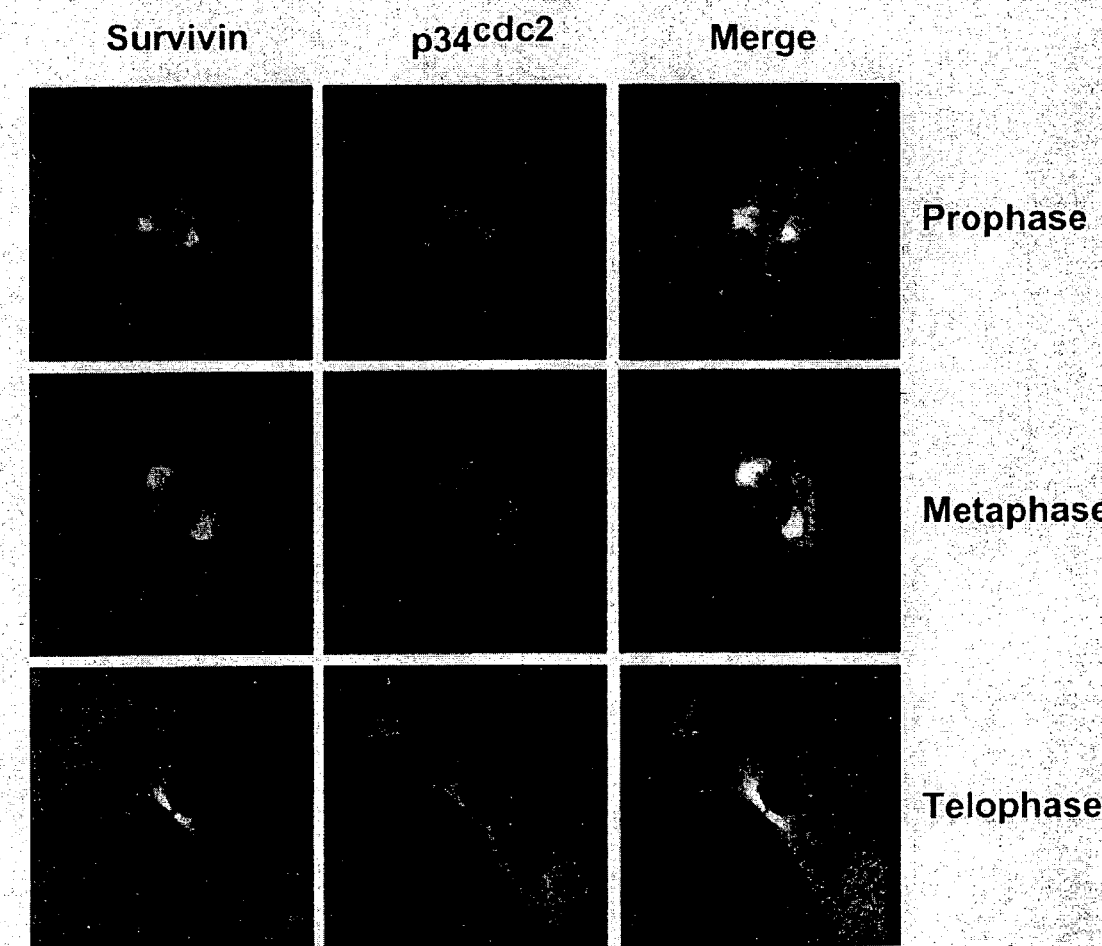

α-β-tubulin

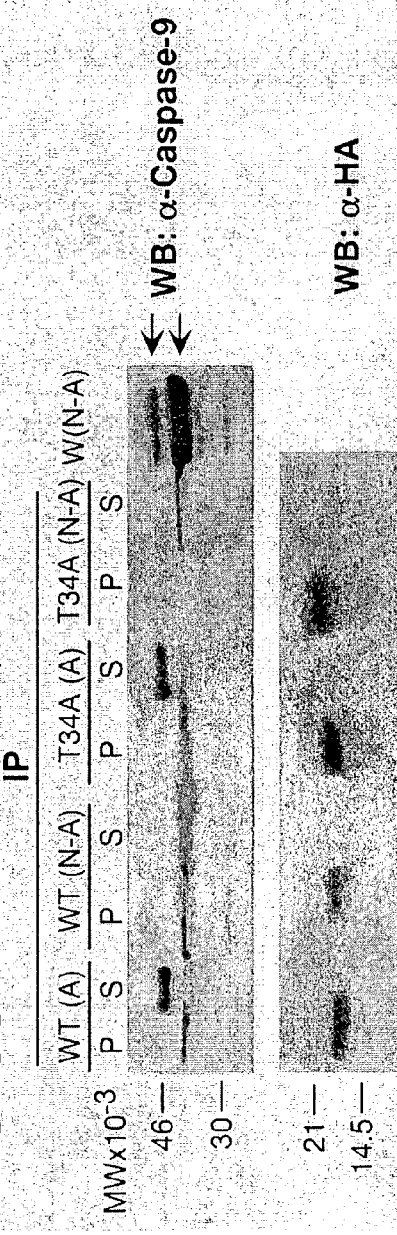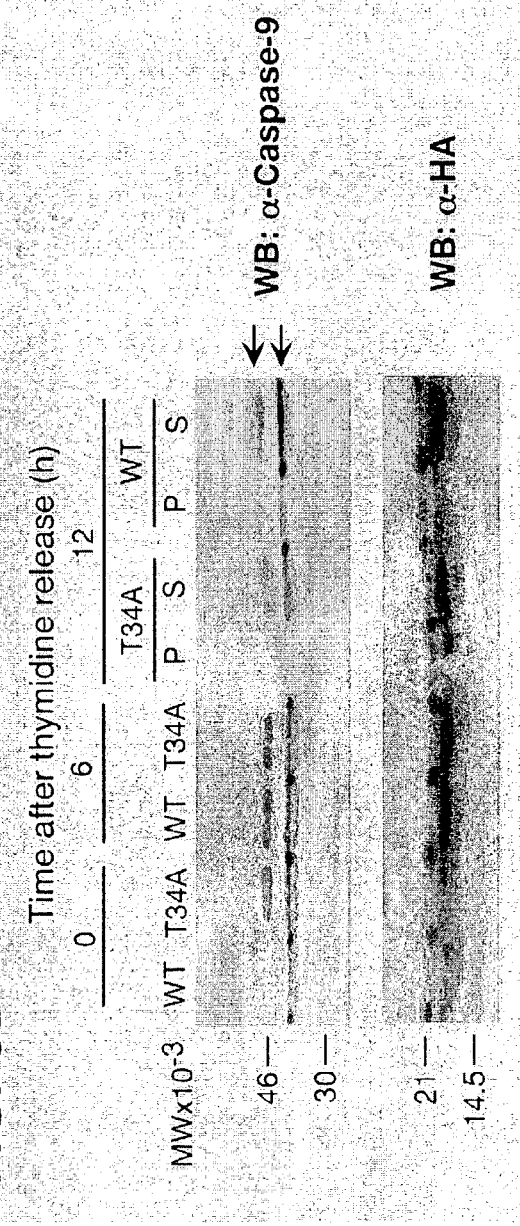

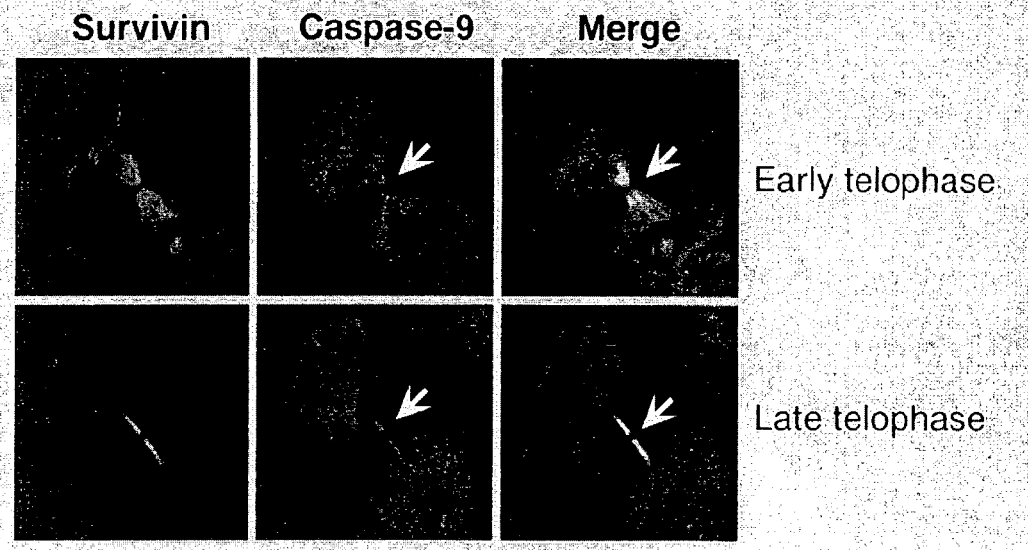
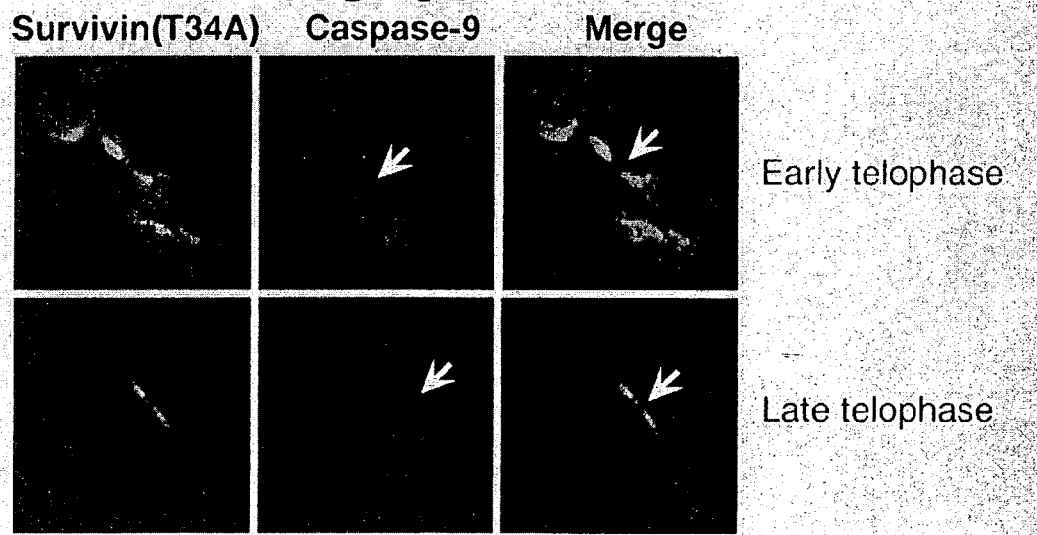
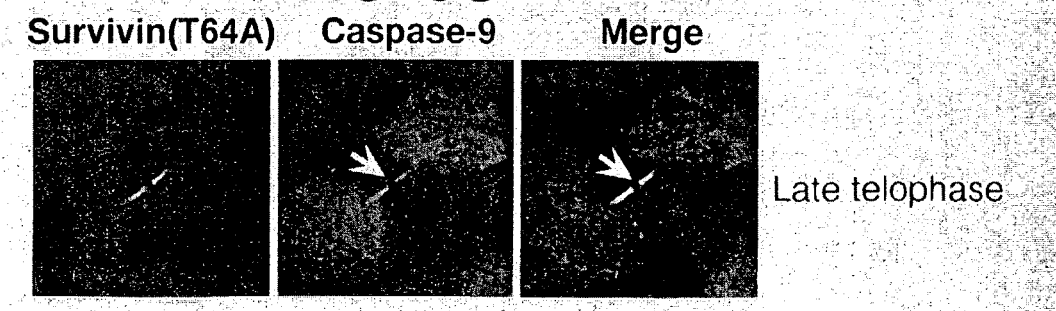

+Tet  −Tet

Tet +  Tet −

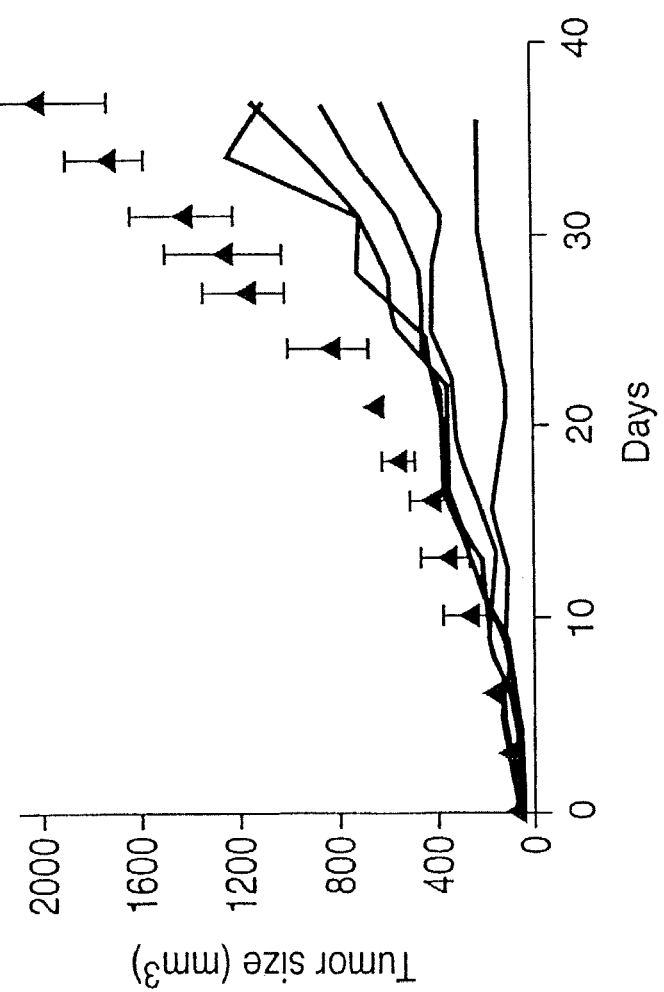
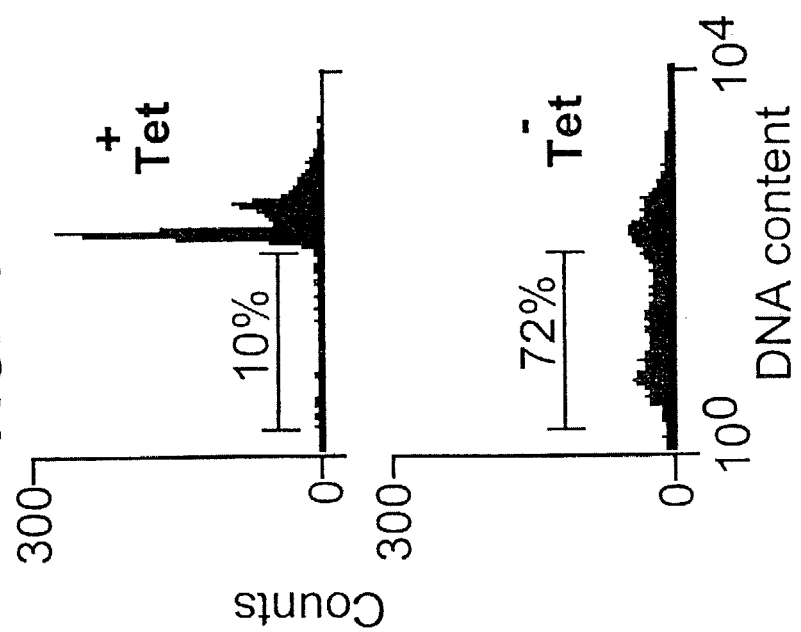

 

METHODS FOR SELECTIVELY MODULATING SURVIVIN APOPTOSIS PATHWAYS

RELATED APPLICATIONS

This application is a divisional of U.S. application Ser. No. 09/515,514, filed Feb. 29, 2000, now U.S. Pat. No. 6,509,162. This application is related to provisional application Ser. No. 60/080,288, filed Apr. 1, 1998, International Application PCT/US99/07205, filed Apr. 1, 1999, application Ser. No. 09/283,144, filed Apr. 1, 1999, provisional application Ser. No. 60/031,435, filed Nov. 20, 1996, application Ser. No. 08/975,080, filed Nov. 20, 1997 and International Application PCT/US97/21880, filed Nov. 20, 1997, all of which are herein incorporated by reference in their entirety.

ACKNOWLEDGMENT OF FEDERAL SUPPORT

The research and discoveries described herein were supported by grants HL 43773 and HL 54131 from the National Institutes of Health.

TECHNICAL FIELD

The present invention, based on the discovery of a new biological phenomena, provides methods and compositions for use in identifying agents that modulate the phosphorylation of survivin, the interaction between survivin and p34$^{cdc2}$cyclin B1 kinase complex, and the interaction between survivin and caspase-9. Related methods and compositions can be used to modulate survivin regulated apoptosis.

BACKGROUND OF THE INVENTION

A. The Role of Survivin in Programmed Cell Death

Programmed cell death (sometimes referred to as apoptosis) is distinguishable, both morphologically and functionally, from necrosis. Programmed cell death is a natural form of death that organisms use to dispose of cells. Cells dying by programmed cell death usually shrink, rarely lyse, and are efficiently removed from the organism (rapidly recognized and engulfed by macrophages) without the appearance of inflammation (Michael Hengartner, "*Cell Death and Aging, Molecular Mechanisms of,*" IN MOLECULAR BIOLOGY AND BIO-TECHNOLOGY 158-62 (ed. R. A. Meyers, 1995)).

Apoptosis was initially used to describe a subset of programmed cell deaths sharing a particular set of morphological features which include membrane blebbing, shrinkage of cytoplasm, chromatic condensation and formation of a "DNA ladder." During apoptosis, cells lose their cell junctions and microvilli, the cytoplasm condenses and nuclear chromatin marginates into a number of discrete masses. While the nucleus fragments, the cytoplasm contracts and mitochondria and ribosomes become densely compacted. After dilation of the endoplasmic reticulum and its fusion with the plasma membrane, the cell breaks up into several membrane bound vesicles, referred to as apoptotic bodies, which are usually phagocytosed by adjacent cells. Activation of particular genes such as tumor suppressor genes in vertebrates is thought to be necessary for apoptosis to occur. Apoptosis induced by numerous cytotoxic agents can be suppressed by expression of the gene bcl-2, which produces a cytoplasmic protein Bcl-2 (THE ENCYCLOPEDIA OF MOLECULAR BIOLOGY 67 (ed. John Kendrew et al., Blackwell Science; Oxford, England, 1994).

Survivin has recently been identified as a novel inhibitor of apoptosis (IAP). The gene encoding survivin is located on chromosome 17q25. Survivin is a 16.5 kD cytoplasmic protein containing a single partially conserved BIR domain, and a highly charged carboxyl-terminus coiled-coil region instead of a RING finger, which inhibits apoptosis induced by growth factor (IL-3) withdrawal when transferred in B cell precursors (Ambrosini, G. et al., 1997). Unlike other members of the IAP family, survivin has only one BIR domain and does not have a carboxy-terminal RING finger. Instead, survivin has a carboxy-terminus coiled-coil region. Based on overall sequence conservation, the absence of a carboxy terminus RING finger and the presence of a single, partially conserved, BIR domain, survivin is the most distantly related member of the IAP family, sharing the highest degree of similarity with NAIP (Roy, N. et al., 1995). Additionally, unlike other IAP proteins, survivin is undetectable in adult tissues, but becomes prominently expressed in all the most common human cancers of lung, colon, breast, pancreas, and prostate, and in ~50% of high-grade non-Hodgkin's lymphomas, in vivo.

Expression of survivin in embryonic and fetal development may contribute to tissue homeostasis and differentiation that is independent of bcl-2 (Adida et al., 1998). Aberrations of this survivin-associated developmental pathway may result in prominent re-expression of survivin in neoplasia and abnormally prolonged cell viability (Adida et al., 1998).

Deregulation of programmed cell death has emerged as a primary mechanism contributing to the pathogenesis of various human diseases including cancer. While the impact of anti-apoptosis genes in neoplasia has focused, for example, on the role of bcl-2 in follicular lymphoma, a potential distribution of IAP proteins, such as survivin, has only begun to be investigated. Survivin is rarely present in adult tissues but has been detected in adenocarcinoma of the pancreas, breast adenocarcinoma, colon cancer, head and neck squamous cell carcinoma, neuroblastoma, malignant thymoma, prostate cancer, and benign prostate hyperplasia (see U.S. Ser. No. 08/975,080, now U.S. Pat. No. 6,245,523). This expression pattern suggests that overexpression of survivin or alterations in survivin gene regulation may commonly occur during tumorigenesis.

B. Cell Cycle

Living organisms are composed of cells, whose growth and division require a regular sequence of events and processes that comprise the cell cycle. Some cell cycle events are continuous (e.g., synthesis of proteins and lipids), whereas others are discontinuous (e.g., DNA synthesis). Two discontinuous processes for cell survival are the replication of DNA and the segregation of chromosomes to the daughters of cell division during mitosis. If either of these steps are performed inaccurately, the daughter cells will be different from each other and will almost certainly be flawed. Segregation of chromosomes occurs during mitosis, normally a relatively brief period in the cell cycle, which culminates in the highly visible act of cell division (e.g., cytokinesis). The remainder of cell cycle comprises interphase, during which growth occurs. Chromosome replication occurs in eukaryotic cells only during interphase; and replication and segregation are mutually exclusive processes.

Interphase is subdivided into the S phase when DNA synthesis occurs and the gaps separating S phase from mitosis. G1 is the gap after mitosis, before DNA synthesis starts; G2 is the gap after DNA synthesis is complete, before mitosis and cell division. Cellular constituents direct the cell cycle by acting as regulatory elements.

C. Checkpoint Mechanisms for Apoptosis and Cell Cycle

One of the central functions of apoptosis (programmed cell death) in maintaining homeostasis is the elimination of damaged and potentially harmful cells (Vaux and Korsmeyer, 1999). For this process to be effective, the apoptotic machinery must constantly couple to surveillance mechanisms, i.e. "checkpoints", sensing DNA damage, adverse environmental conditions, and oncogene or viral transformation (Hunter, 1997; Paulowich et al., 1997). Checkpoint activation under these conditions initiates apoptosis (Evan and Littlewood, 1998) via the assembly of an evolutionary conserved "apoptosome", which in mammalian cells comprises an upstream cell death protease, caspase-9, the adapter/cofactor protein Apaf-1, mitochondria-derived cytochrome c and dATP/ATP (Green, 1998). Although it is debated how apoptosome assembly promotes caspase-9 catalytic activity (Rodriguez and Lazebnik, 1999; Zou et al., 1999), this process culminates with downstream activation of effector caspases and cleavage of critical cellular substrates (Salvesen and Dixit, 1997; Thornberry and Lazebnik, 1998). A similar paradigm linking apoptosis control to checkpoint activation (Levine, 1997), has been extended to surveillance mechanisms presiding over cell cycle transitions (Pines, 1999), assembly of a bipolar mitotic apparatus (Merdes and Cleveland, 1997), preservation of ploidy (Nicklas, 1997), and timing of cytokinesis (Field et al., 1999). In this context, dysregulated expression of apoptosis inhibitors bcl-2 and bcl-$x_L$ has been shown to restrain S phase entry (Linette et al., 1996), promote cell cycle exit (Huang et al., 1997), and cause aneuploidy (Minn et al., 1996), further demonstrating a role of the apoptotic machinery in cell cycle progression.

Survivin is expressed in G2/M in a cell cycle-dependent manner, and localized to mitotic spindle microtubules and intercellular acto-myosin bridges, i.e. midbodies, during cell division (Li et al., 1998). Interference with this topography, or blocking survivin expression, caused increased caspase-3 activity in G2/M (Li et al., 1998), and a profound dysregulation of mitotic progression (Li et al., 1999), suggesting that survivin may regulate a novel apoptotic checkpoint at cell division. This pathway was dramatically exploited in cancer (Ambrosini et al., 1997), where survivin was identified as one of the top four "transcriptomes" out of 3.5 millions mRNAs, uniformly expressed in cancer, but not in normal tissues (Velculescu et al., 1999). Additionally, it has been shown that transformed cells are exquisitely sensitive to manipulation at this mitotic checkpoint as interference with survivin expression and function using dominant-negative mutants with point mutations in the conserved baculovirus IAP repeat (BIR) domain or survivin antisense resulted in aberrant mitoses (Li et al., 1999) and spontaneous apoptosis (Ambrosini et al., 1999; Grossman et al., 1999a; Grossman et al., 1999b). This phenotype is unique to survivin and not observed with other apoptosis inhibitors potentially contributing to neoplasia, as antisense inhibition of Bcl-2 increased sensitivity to apoptosis but did not in itself induce cell death (Jansen et al. 1998).

The present invention identifies a mechanism by which survivin may integrate the control of cell division with the regulation of apoptosis in mammalian cells. The present invention also provides two classes of survivin antagonists that modulate the expression of survivin and interfere with the antiapoptotic survivin pathway in melanoma tumors in vivo. Further, the present invention provides a method of inhibiting the growth of tumor comprising administering an effective amount of a survivin antagonist to the tumor.

SUMMARY OF THE INVENTION

The present invention is based in part on the finding that survivin is phosphorylated by the main mitotic kinase complex, p34$^{cdc2}$-cyclin B1 (Nurse, 1994), and that this process is essential to preserve viability of cells traversing mitosis.

The present invention is also based in part on the finding that lack of survivin phosphorylation by p34$^{cdc2}$ causes dissociation of the survivin-active caspase-9 complex, selective mislocalization of caspase-9 from midbodies, and caspase-9-dependent apoptosis of cells traversing mitosis.

The present invention provides a method of identifying an agent that modulates the phosphorylation of survivin comprising the steps of incubating survivin and p34$^{cdc2}$-cyclin B1 kinase complex with an agent and determining whether the agent modulates the phosphorylation of survivin, thereby identifying an agent that modulates phosphorylation of survivin.

The present invention further provides methods of identifying an agent that modulates the interaction of survivin and p34$^{cdc2}$-cyclin B1 kinase complex.

The invention also provides methods of modulating the interaction between survivin and p34$^{cdc2}$-cyclin B1 kinase complex comprising the step of administering an effective amount of an agent which modulates at least one interaction between Survivin and p34$^{cdc2}$-cyclin B1 kinase complex.

The invention further includes methods of modulating apoptosis in a cell, comprising administering to the cell an effective amount of an agent that modulates the interaction between survivin and p34$^{cdc2}$-cyclin B1 kinase complex. The invention further provides agents, compositions, and peptides that modulate the interactions between Survivin and p34$^{cdc2}$-cyclin B1 kinase complex.

The present invention also provides a method of identifying agents that modulate the interaction between phosphorylated survivin and caspase-9. The invention further provides agents, compositions, and peptides that modulate the interactions between phosphorylated survivin and caspase-9.

The present invention provides survivin antagonists such as the dominant negative survivin mutant (Thr$^{34}$→Ala) and survivin antisense nucleic acid, to modulate the expression of survivin in a cell. The invention also discloses using the survivin antagonists to inhibit the growth of tumors in vivo and in vitro.

BRIEF DESCRIPTION OF THE DRAWINGS

FIGS. 1A-D. p34$^{cdc2}$cyclin B1 phosphorylation of survivin on Thr$^{34}$.

FIG. 1A shows clustal alignment of survivin and IAP proteins (SEQ ID NO: 11-21). A consensus p34$^{cdc2}$ phosphorylation sequence (S/TPXR/K, SEQ ID NO: 11) surrounding Thr$^{34}$ in survivin is boxed.

FIG. 1B. In vitro kinase assay. Wild type (WT) survivin, survivin(T34A) (T34A), or control (H1) were incubated with baculovirus-expressed p34$^{cdc2}$-cyclin B1 or cdk2-cyclin E in kinase buffer plus 10 µCi γ-$^{32}$P-ATP for 30 min at 30° C. Samples were separated by SDS gel electrophoresis and radioactive bands were visualized by autoradiography. Equal protein loading was confirmed by Coomassie blue staining of the gel.

FIG. 1C shows reactivity with an antibody to phosphorylated survivin Thr$^{34}$. The experimental conditions for kinase assays are the same as in B, except that samples were immunoblotted with an antibody raised against the survivin peptide sequence L$^{28}$ EGCACT*PERMAEAGFI$^{44}$ SEQ ID NO: 1 containing phosphorylated Thr$^{34}$(T*), and sequentially affinity purified on non-phosphorylated/phosphorylated peptide-Sepharose columns (-phosph. T34), or with an antibody raised against recombinant survivin (-survivin) (Grossman et al., 1999).

FIG. 1D shows in vivo phosphorylation of survivin. HeLa cells were transfected with HA-survivin, labeled with 200 µCi/ml $^{32}$Pi in phosphate-free DMEM medium and immunoprecipitated with control IgG or anti-HA antibody with visualization of radioactive bands by autoradiography. Experiments were repeated at least three times with comparable results. For all panels, relative molecular weight markers are indicated on the left.

FIGS. 2A-C. Physical association between survivin and p34$^{cdc2}$.

FIG. 2A shows cyclin-dependent kinase immunoprecipitation. HeLa cells asynchronously growing (Async.) or synchronized to G1, S, or G2/M were detergent-solubilized and immunoprecipitated with antibodies to p34$^{cdc2}$ (left panel), or Cdk2 (right panel). Samples were electrophoresed, transferred to nylon 34 membranes and separately immunoblotted with antibodies to survivin, p34$^{cdc2}$ or Cdk2, respectively.

FIG. 2B shows survivin immunoprecipitation. The experimental procedures are the same as in A, except that asynchronously growing HeLa cells were transfected with HA-survivin or HA-survivin(T34A), immunoprecipitated with an antibody to HA, and immunoblotted with antibodies to p34$^{cdc2}$ or HA. W, whole HeLa cell extract.

FIG. 2C shows co-localization of survivin and p34$^{cdc2}$, in vivo. HeLa cells on optical grade glass coverslips were fixed in acetone/methanol and simultaneously incubated with mAb 8E2 to survivin and a rabbit antibody to p34$^{cdc2}$, followed by FITC-conjugated goat anti-mouse (survivin) and TR-conjugated goat anti-rabbit (p34$^{cdc2}$) antibodies. Images were analyzed by confocal laser-scanning microscopy at the indicated cell cycle phases. Image merging analysis is shown on the right of each panel. For panels A and B, relative molecular weight markers are indicated on the left.

FIG. 3A shows nuclear morphology. HeLa cells transfected with GFP-vector (vector), GFP-survivin(T34A) (T34A), or GFP-caspase-9 (Met$^1$-Asp$^{330}$) (caspase-9), were scored morphologically for nuclear integrity by DAPI staining after 48-h. Arrows, nuclear fragmentation and chromatin condensation in GFP-expressing cells.

FIG. 3B shows summary of HeLa cell apoptosis induced by expression of survivin(T34A). The experimental procedures are the same as in A. Data are the meavSEM of four independent experiments.

FIG. 3C shows caspase-dependent apoptosis induced by survivin(T34A). HeLa cells were transfected with GFP-survivin(T34A) in the presence or in the absence of 20 µM of the caspase inhibitor, Z-VAD-fmk. Gated GFP-expressing cells were analyzed 48 h after transfection for DNA content by propidium iodide staining and flow cytometry. The percentages of apoptotic cells with sub-G1 (hypodiploid) 35 DNA content are indicated. Apoptotic HeLa cells in GFP-vector transfectants were 8%. Data are representative of one experiment out of at least three independent determinations.

FIG. 3D shows aberrant mitoses. HeLa cells transfected with wild type survivin (WT) or survivin(T34A) (T34A), were fixed in microtubule-stabilizing buffer (Li et al., 1998), and labeled with mAb 20C6 to ⇓-tubulin followed by FITC-conjugated goat anti-mouse IgG. Images were analyzed by confocal microscopy as described in FIG. 2C.

FIG. 4A shows tet-regulated YUSAC-2 transfectants. Three YUSAC-2 melanoma cell lines stably transfected with survivin(T34A) in pTet splice were analyzed for DNA content by propidium iodide staining and flow cytometry in the presence (Tet+) or absence (Tet-) of Tet. The percentages of cells with sub-G1 (apoptotic) DNA content after a 3-d culture at 37° C. are indicated.

FIG. 4B shows TUNEL labeling. The experimental conditions are the same as in A, except that a subclone of YUSAC-2 transfectants, F5.C4 was analyzed in the presence (Tet+) or in the absence (Tet-) of Tet for internucleosomal DNA fragmentation by end-labeling with terminal deoxynucleotidyl transferase (TdT) and a peroxidase-conjugated anti-digoxigenin antibody.

FIG. 4C shows cell cycle analysis. F5.C4 cells were synchronized at the G1/S boundary in the presence (Tet+) or absence (Tet-) of Tet, released, and analyzed for changes in DNA content at 3-h intervals by propidium iodide staining and flow cytometry. The percentages of cells with sub-G1 (apoptotic), G1, S, or G2/M DNA content are indicated for each time point analyzed. Data are representative of one experiment out of at least three independent determinations.

FIGS. 5A-D. Thr$^{34}$ phosphorylation changes the specificity of survivin-caspase-9 interaction at mitosis.

FIG. 5A shows phosphorylation-independent association of survivin-proform caspase-9 in interphase cells. Asynchronously growing HeLa cells were transfected with HA-wild type survivin (WT) or HA-survivin(T34A) (T34A), detergent-solubilized after 24 h and immunoprecipitated with an antibody to HA followed by Western blotting with an antibody to caspase-9. Arrow, position of 46 kDa proform caspase-9.

FIG. 5B shows specificity of survivin-caspase-9 interaction. The experimental conditions are the same as in A, except that HA-survivin and HA-survivin(T34A) immunoprecipitates were separately immunoblotted with antibodies to caspase-8 or HA. S, supernatant of HA-survivin immunoprecipitate. Arrow, position of ~55 kDa proform caspase-8.

FIG. 5C shows modulation of survivin-caspase-9 interaction in cycling cells. The experimental conditions are the same as in A, except that extracts from adherent (A) or non-adherent (N-A), i.e. mitotic/apoptotic, HeLa cells were harvested 48-h after transfection. Aliquots of the immunoprecipitates (pellet, P) or their supernatants (S) were immunoblotted with antibodies to caspase-9 or HA. Arrows, position of 46 kDa proform caspase-9 and ~35 kDa active caspase-9. W, whole extract from mitotic/apoptotic HeLa cells.

FIG. 5D shows phosphorylation-dependent modulation of survivin-active caspase-9 recognition at mitosis. HeLa cells were transfected with the indicated HA-constructs, synchronized to the G1/S boundary by a 16-h treatment with thymidine and released. Aliquots of the various cultures were immunoprecipitated at the indicated time intervals with an antibody to HA, and immunoblotted with antibodies to caspase-9 or HA. P, pellet; S, supernatant. For all panels, molecular weight markers are indicated on the left. For all panels, experiments were repeated at least twice with comparable results.

FIGS. 6A-C. Expression of survivin(T34A) mislocalizes caspase-9 from midbodies at telophase.

HeLa cells transfected with HA-wild type survivin (Survivin) (A), survivin(T34A) (B), or survivin(L64A) (C) were labeled with a mAb to HA (A, B) or mAb 8E2 (C) and a rabbit antibody to caspase-9. Binding of the primary antibodies was detected by addition of FITC-conjugated goat anti-mouse (survivin) or TR-conjugated anti-rabbit (caspase-9) antibody, and analyzed by confocal microscopy. Image merging analysis of the individual staining is shown on the right of each panel. Arrows, localization of wild type/mutant survivin and caspase-9 at midbodies at telophase. Experiments were repeated at least four times with comparable results.

Figure 7A:
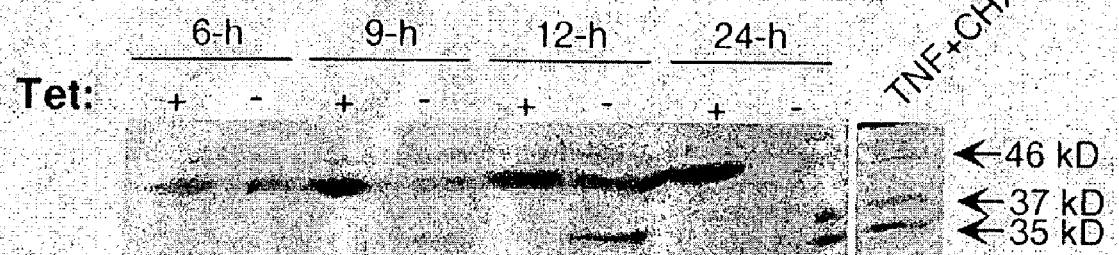
Figure 7B:
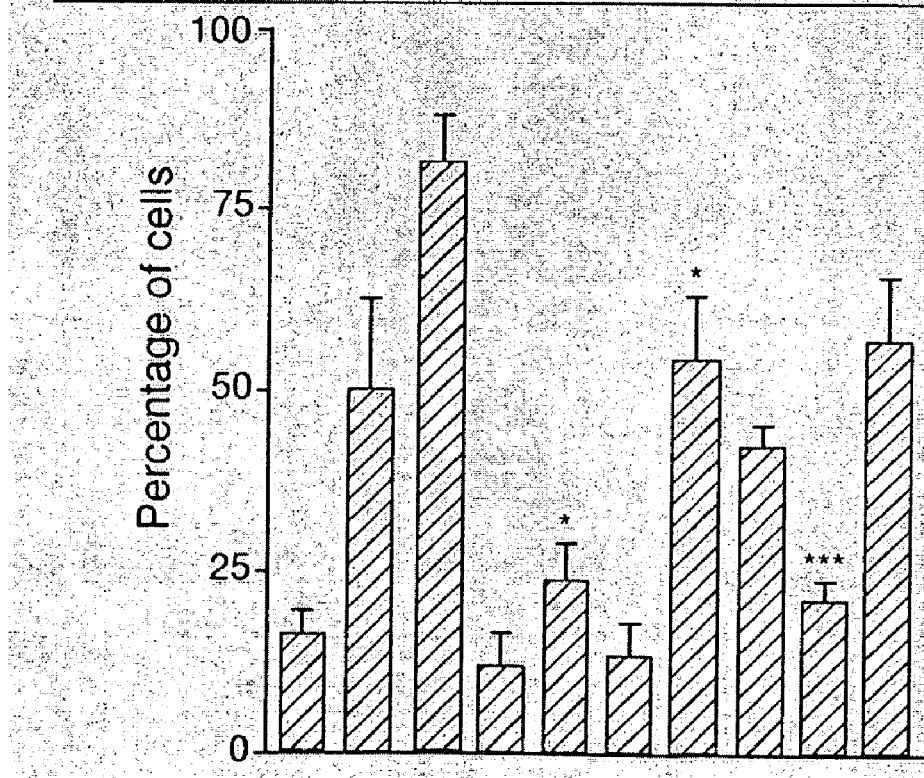

FIGS. 7A-B. Caspase-9 dependent apoptotic checkpoint at cell division.

FIG. 7A shows proteolytic activation of caspase-9 at mitosis. Tet+ and Tet− F5.C4 cells characterized as described in FIG. 4, were harvested at the indicated time intervals after thymidine release and immunoblotted with an antibody to caspase-9. TNF+CHX, extract of HeLa cells treated with 10 ng/ml TNFα plus 10 µg/ml cycloheximide. Arrows, position of ~46 kDa proform caspase-9, and ~35 kDa and ~37 kDa active caspase-9 bands.

FIG. 7B shows effect of caspase-9(C287A) dominant negative mutant on apoptosis induced by survivin(T34A). HeLa cells were transfected with the various indicated combinations of GFP-constructs, with or without etoposide (10 µg/ml) or TNFα (10 ng/ml) plus cycloheximide (10 µg/ml), harvested after 48 h, and GFP-labeled cells were morphologically scored for nuclear fragmentation by DAPI staining, as described in FIG. 2B. DN, dominant negative. Data are the mea±SEM of four independent experiments.

FIGS. 8A-D. Tet-regulated induction of survivin BIR mutant, apoptosis in F5.C4 cells, and tumor formation in CB.17 mice.

Figure 8A:
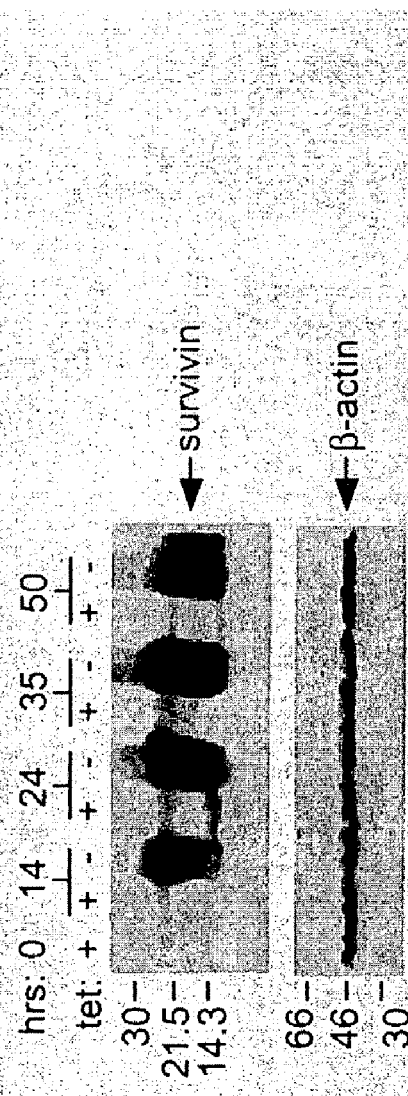

FIG. 8A shows F5.C4 cells were cultured in the presence or absence of tet (0.5 µg/ml) and harvested at the indicated time intervals. Lysates were subjected to Western blotting with antibodies to survivin (top panel) or β-actin (bottom panel) as described (Grossman et al., 1999). Given the massive expression of the BIR mutant, autoradiography exposure time was limited in order to visualize discreet bands. The endogenous wild-type survivin protein in uninduced (+tet) cells is not apparent at this level of exposure, but was apparent at longer exposure times.

Figure 8B:
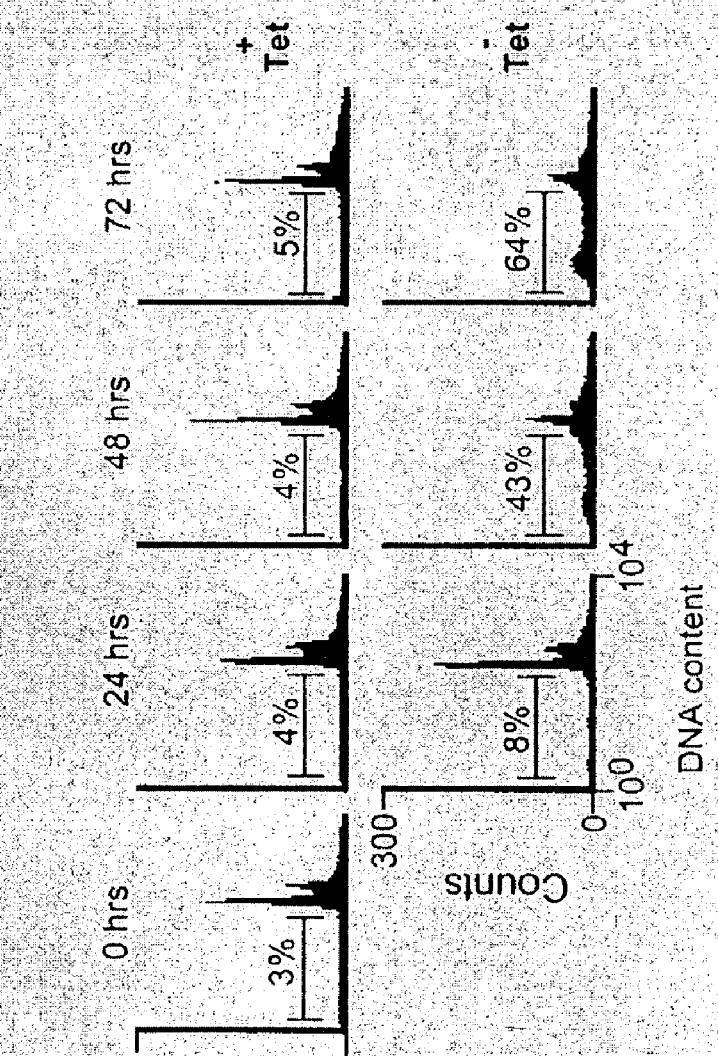

FIG. 8B shows F5.C4 cells were cultured in the presence or absence of tet for the indicated time intervals, and both non-adherent and adherent cells were recovered. Cells were then fixed, permeabilized and stained with propidium iodide for DNA content as described (Grossman et al., 1999). The marker indicates the sub-$G_1$ fraction, corresponding to apoptotic cells.

Figure 8C:
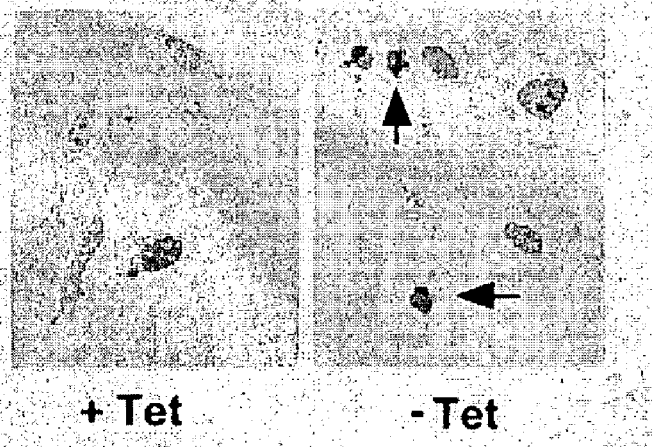

FIG. 8C shows F5.C4 cells were plated on coverslips treated with 2% gelatin (Sigma), and incubated 48 hours in the presence or absence of tet. Cells were fixed in 1% paraformaldehyde for 10 minutes at room temperature and then permeabilized with acetic acid and ethanol for 5 minutes at −200° C. Arrows indicate TUNEL-reactive (Shockett et al., 1995) cells with apoptotic morphology.

Figure 8D:

FIG. 8D shows YUSAC-2 parental cells ($3 \times 10^6$, top panel) or F5.C4 cells transfected with the survivin Thr$^{34}$ →Ala mutant (bottom panel) were injected subcutaneously into CB.17 mice, and tet (100 µg/ml) was added (left side of panels) or withheld (right side of panels) from the drinking water as indicated. Photographs were taken of representative 8 weeks following injection.

Figure 9A:
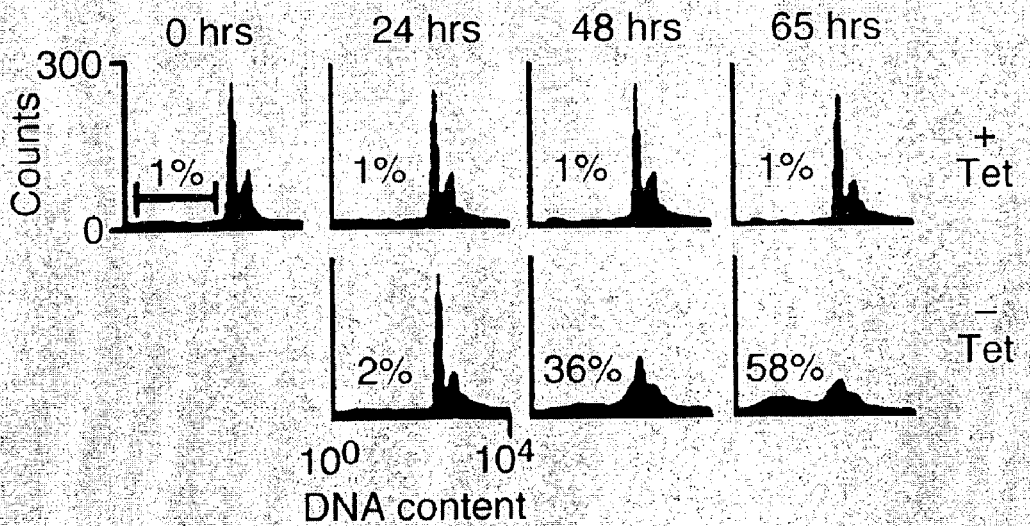
Figure 9B:
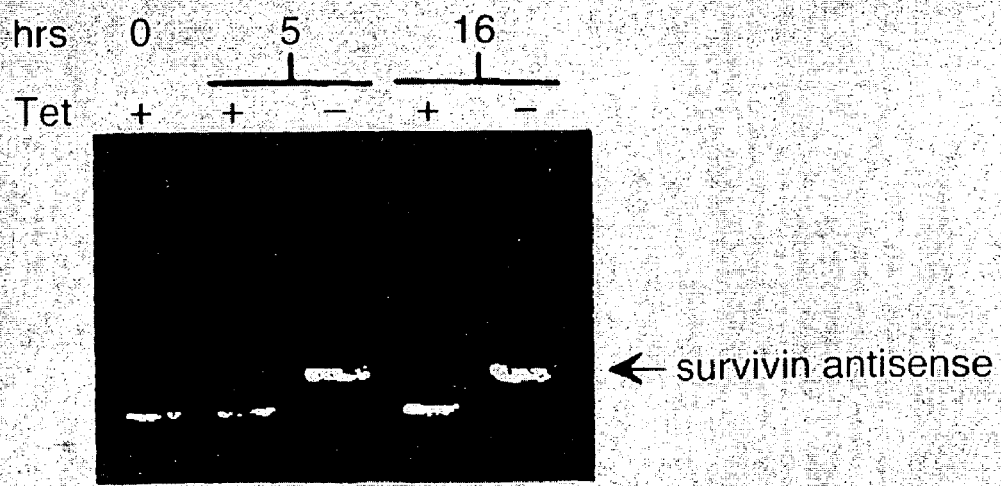

FIGS. 9A-B. In vitro characterization of survivin antisense-transfected subclone B8.

FIG. 9A shows DNA content analysis, performed as described in FIG. 1.

FIG. 9B shows RT-PCR analysis of cells cultured in the presence or absence of tet as indicated. RNA prepared using TriReagent, and reverse transcription primed with a survivin sense primer.

FIGS. 10A-B. Effect of survivin BIR mutant expression in established tumors in vivo, and tet– regulated apoptosis of tumor lines re-established in vitro.

FIG. 10A shows growth of F5.C4 tumors in 5 animals maintained on tet (closed triangles). Error bars indicate standard deviation. Also shown are 5 representative growth curves from 15 animals in which tet was withheld (day 0) upon tumor formation (no symbols).

FIG. 10B shows a representative F5.C4 tumor following removal of tet was expanded in vitro in the presence of G418 and tet (27), and then after culturing for 72 hours in the presence (top panel) or absence (bottom panel) of tet was examined for DNA content as in FIG. 1.

FIGS. 11A-B. Histologic analysis of YUSAC-2 tumor.

Tumor formed by untransfected YUSAC-2 cells was stained with (A) hematoxylin and eosin and (B) HMB-45 antibody.

Figure 12A:
Figure 12B:
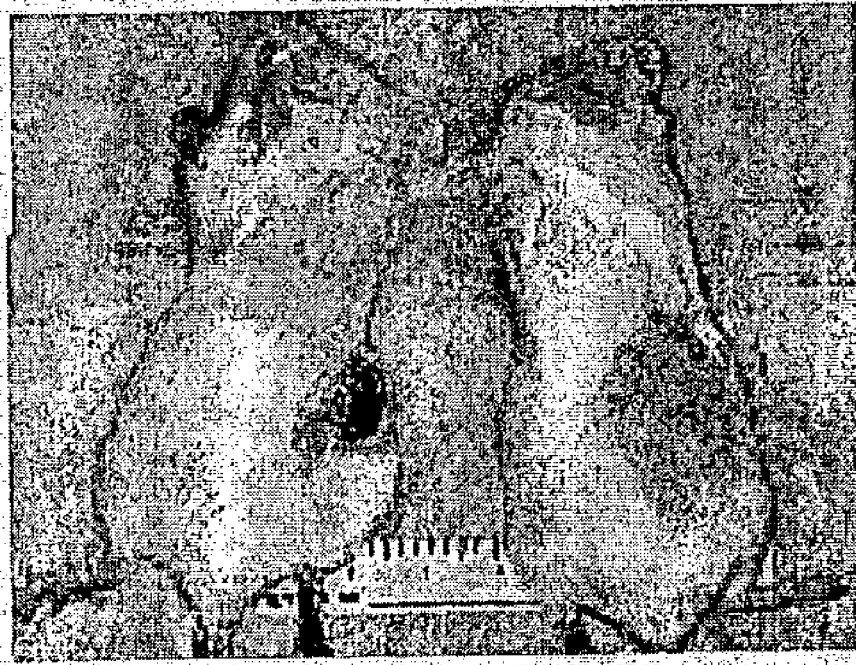

FIG. 12. Tumor Formation in CB.17 Mice with F5.E5 Cells.

F5.E5 cells ($3 \times 10^6$, top panel) or B8 cells (bottom panel) were injected subcutaneously into CB.17 mice, and tet (100 mg/ml) was added (left side of panels) or withheld (right side of panels) from the drinking water.

Figure 13:
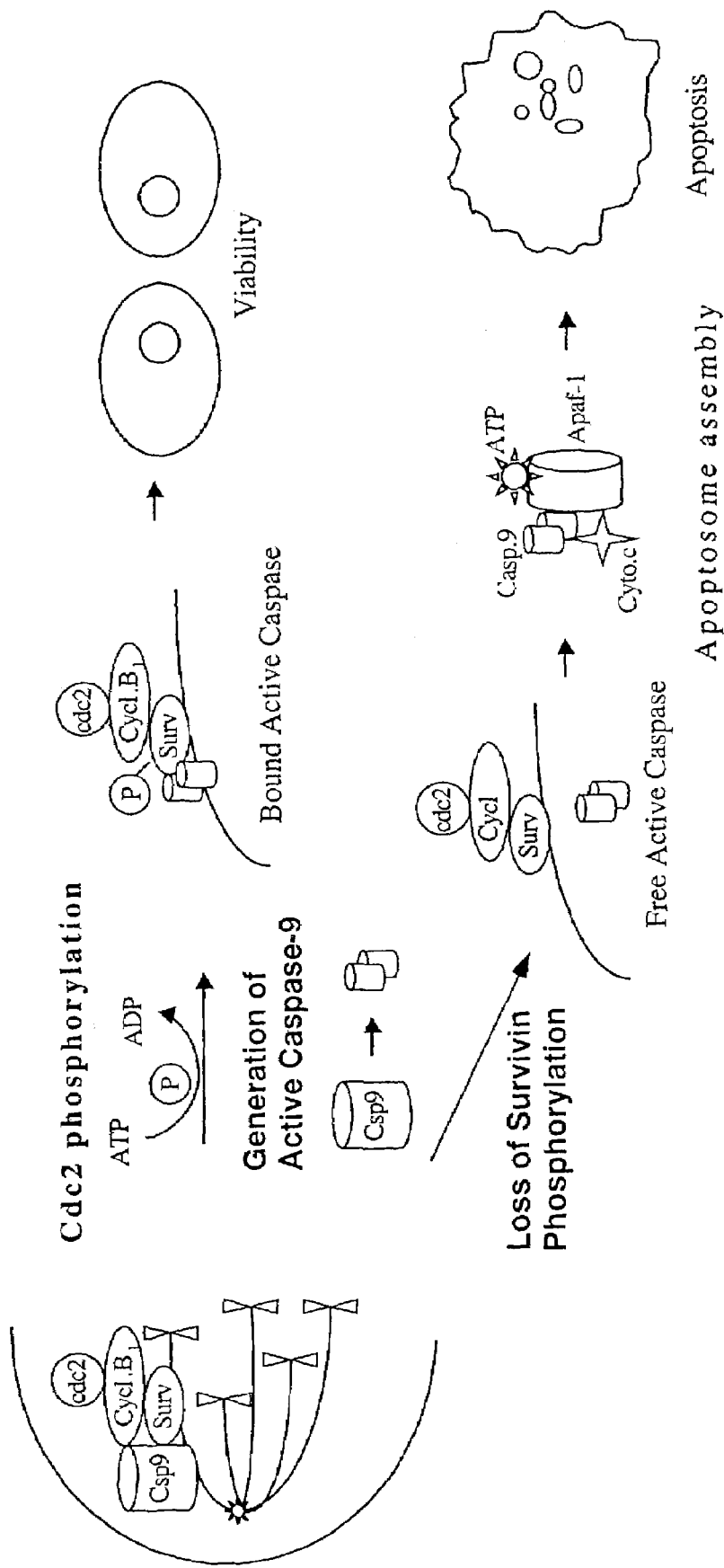

FIG. 13. Summary of the Role of Survivin during Cell Cycle Progression.

A schematic diagram disclosing the role of survivin during cell cycle progression.

DETAILED DESCRIPTION OF THE INVENTION

I. General Description

The present invention is based in part on the finding that survivin is phosphorylated by the main mitotic kinase complex, p34$^{cdc2}$-cyclin B1 (Nurse, 1994), and that this process is essential to preserve viability of cells traversing mitosis.

The present invention is also based in part on the finding that survivin binds to p34$^{cdc2}$-cyclin B1 kinase complex. Moreover, the present invention is based in part on the finding that phosphorylated survivin interacts with caspase-9.

The phosphorylation of survivin protein by p34$^{cdc2}$-cyclin B1 kinase complex, the binding of survivin to the kinase complex, and the binding of survivin to caspase-9 can be used to identify agents, or serve as a target for agents, that inhibit or stimulate survivin mediated functions. The agents may be used to modulate survivin mediated inhibition of cellular apoptosis, to block abnormal cell growth or to extend cell growth in culture. As used herein, modulation of apoptosis means increasing or decreasing the number of cells that would otherwise undergo apoptosis in a given cell population. This can be effected by modulating (increasing or decreasing) phosphorylation of survivin by p34$^{cdc2}$-cyclin B1 kinase complex, the binding of survivin to the kinase complex, or the binding of phosphorylated survivin to caspase-9. Preferably, the given cell population in which apoptosis is to be modulated is found in a tumor or other tissue or group of cells in which beneficial effects result from the modulation. Preferably, the increase or decrease in number of cells that would otherwise undergo apoptosis in a given cell population is at least about 10%, 20%, 40% or more preferably at least about 50% of the cells in that population.

Additionally, the present invention is based in part on the finding that survivin antagonists such as dominant negative survivin mutant (Thr$^{34}$→Ala) and antisense survivin nucleic acids inhibit the expression of endogenous survivin in a melanoma and inhibits the growth of the melanoma in vivo and in vitro. Accordingly, the present invention is also based in part on the finding that administering an effective amount of a survivin antagonist to tumors inhibits the growth of tumors.

II. Specific Embodiments

A. Methods to Identify Agents that Modulate or Block Phosphorylation of Survivin by, Binding of Survivin to p34$^{cdc2}$-Cyclin B1 Kinase Complex, or Binding of Survivin to Caspase-9

As set forth above, the present invention provides method for identifying agents that modulate, reduce, or block the phosphorylation of survivin by p34$^{cdc2}$-cyclin B1 kinase complex. The present invention also provides methods for identifying agents that, modulate, reduce or block the association of survivin with p34$^{cdc2}$-cyclin B1 kinase complex. The present invention also provides methods for identifying agents that modulate reduce or block the association of survivin to caspase-9.

In one assay format, survivin is mixed with p34$^{cdc2}$-cyclin B1 kinase complex in the presence and absence of an agent to be tested. After mixing under conditions that allow association of survivin with the kinase complex, the two mixtures are analyzed and compared to determine if the agent modulated, increased, promoted, reduced or blocked the phosphorylation of survivin or the binding of survivin to the p34$^{cdc2}$-cyclin B1 kinase complex. Likewise in the assay for phosphorylated survivin/caspase-9 or unphosphorylated survivin/caspase-9 (See Example 3), phosphorylated survivin is mixed with caspase-9 or unphosphorylated survivin is mixed with either proform/active caspase-9 of ~46 kDa and ~35 kDa, respectively, in the presence and absence of a test agent to determine if the agent modulated, increased, promoted, reduced or blocked the interaction of the two proteins.

Agents that block or reduce the association of survivin with the p34$^{cdc2}$-cyclin B1 kinase complex or association of survivin and caspase-9 may be identified by their ability to decrease the amount of association present in the sample containing the test agent. Agents that block or reduce the phosphorylation of survivin by p34$^{cdc2}$-cyclin B1 kinase complex may be identified by their ability to decrease the amount of survivin in the sample containing the test agent.

As used herein, an agent is said to reduce or block the phosphorylation of survivin by p34$^{cdc2}$-cyclin B1 kinase complex when the presence of the agent decreases the amount of survivin or totally blocks the phosphorylation of survivin. One class of agents will reduce or block the phosphorylation of survivin by binding to the p34$^{cdc2}$-cyclin B1 kinase complex while another class of agents will reduce or block the phosphorylation of survivin by binding to survivin.

As used herein, an agent is said to reduce or block survivin/p34$^{cdc2}$-cyclin B1 kinase complex association when the presence of the agent decreases the extent to which or prevents the kinase complex from becoming associated with survivin. One class of agents will reduce or block the association by binding to the p34$^{cdc2}$-cyclin B1 kinase complex while another class of agents will reduce or block the association by binding to survivin.

As used herein, an agent is said to reduce or block phosphorylated survivin/caspase-9 complex or unphosphorylated survivin/procaspase-9 complex association when the presence of the agent decreases the extent to which or prevents the caspase from becoming associated with survivin. One class of agents will reduce or block the association by binding to caspase-9 or procaspase-9 while another class of agents will reduce or block the association by binding to survivin.

Agents that are assayed in the above methods can be randomly selected or rationally selected or designed. As used herein, an agent is said to be randomly selected when the agent is chosen randomly without considering the specific sequences involved in the association of survivin with the p34$^{cdc2}$-cyclin B1 kinase complex or survivin with caspase-9. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. As described above, there are at least two sites of action for agents that block survivin/p34$^{cdc2}$-cyclin B1 kinase complex interaction and survivin/caspase-9 interaction: the binding partner contact site on survivin and the survivin contact site on the kinase complex or on caspase-9. Agents can be rationally selected or rationally designed by utilizing the peptide sequences that make up the contact sites of survivin/p34$^{cdc2}$-cyclin B1 kinase complex and of survivin/caspase-9 complex. For example, a rationally selected peptide agent can be a peptide whose amino acid sequence is identical to the survivin contact site on the kinase complex or on caspase-9. Such an agent will reduce or block the association of survivin with the kinase complex by binding to the p34$^{cdc2}$-cyclin B1 kinase complex or the association of survivin by binding to caspase-9.

The agents of the present invention can be, as examples, peptides, small molecules, vitamin derivatives, as well as carbohydrates. A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of survivin, the p34$^{cdc2}$-cyclin B1 kinase complex, or caspase-9. Antibodies may be obtained by immunization of suitable mammalian subjects with peptides, containing as antigenic regions, those portions of the survivin or binding partner, intended to be targeted by the antibodies. Critical regions include the contact sites involved in the association of survivin with the kinase complex, particularly, the region spanning amino acid residue 34 of survivin.

As used herein, survivin protein (or survivin) refers to a protein that has the amino acid sequence of human survivin depicted in Ambrosini et al. (1997). The term "survivin protein" also includes naturally occurring allelic variants of survivin and naturally occurring proteins that have a slightly different amino acid sequence than that specifically recited above. Allelic variants, though possessing a slightly different amino acid sequence than those recited above, will still have the requisite ability to inhibit cellular apoptosis.

As used herein, the survivin family of proteins refers to survivin proteins that have been isolated from organisms in addition to humans. The methods used to identify and isolate other members of the survivin family of proteins are readily available and described in application Ser. No. 08/975,080, now U.S. Pat. No. 6,245,523.

The survivin proteins used in the assays or other embodiments of the present invention are preferably in isolated from. As used herein, a protein is said to be isolated when physical, mechanical or chemical methods are employed to remove the survivin protein from cellular constituents that are normally associated with the survivin protein. A skilled artisan can readily employ standard purification methods to obtain an isolated survivin protein.

The survivin proteins used in the present invention further include conservative variants of the survivin proteins herein described. A conservative variant refers to alterations in the amino acid sequence that do not adversely affect the ability of the survivin protein to bind to a survivin binding partner, such as $p34^{cdc2}$-cyclin B1 kinase complex and caspase-9, and/or to inhibit cellular apoptosis. A substitution, insertion or deletion is said to adversely affect the survivin protein when the altered sequence prevents the survivin protein from associating with a survivin binding partner and/or prevents the survivin protein or survivin protein from inhibiting cellular apoptosis. For example, the overall charge, structure or hydrophobic/hydrophilic properties of survivin can be altered without adversely affecting the activity of survivin. Accordingly, the amino acid sequence of survivin can be altered, for example to render the peptide more hydrophobic or hydrophilic, without adversely affecting the activity of survivin.

The allelic variants, the conservative substitution variants and the members of the survivin family of proteins retain the ability to inhibit cellular apoptosis. Such proteins will ordinarily have an amino acid sequence having at least about 75% amino acid sequence identity with the human survivin sequence, more preferably at least about 80%, even more preferably at least about 90%, and most preferably at least about 95%. Identity or homology with respect to such sequences is defined herein as the percentage of amino acid residues in the candidate sequence that are identical with the known peptides, after aligning the sequences and introducing gaps, if necessary, to achieve the maximum percent homology, and including any conservative substitutions as being homologous. N-terminal, C-terminal or internal extensions, deletions, or insertions into the peptide sequence shall not be construed as affecting homology.

Homology or identity as used above is determined by BLAST (Basic Local Alignment Search Tool) analysis using the algorithm employed by the programs blastp, blastn, blastx, tblastn and tblastx (Karlin, et al. Proc. Natl. Acad. Sci. USA 87: 2264-2268 (1990) and Altschul, S. F. J. Mol. Evol. 36: 290-300 (1993), fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (Nature Genetics 6: 119-129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff, et al. Proc. Natl. Acad. Sci. USA 89: 10915-10919 (1992), fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively.

The present invention also includes the use of survivin mimetics. Survivin mimetics are compounds that mimic the activity of survivin peptides. They are structurally similar to survivin peptides but have a chemically modified peptide backbone. Survivin mimetics may have significant advantages over polypeptide embodiments, including, for example: more economical production; greater chemical stability; enhanced pharmacological properties (half-life, absorption, potency, efficacy, etc.); altered specificity (e.g., a broad-spectrum of biological activities); reduced antigenicity; and others.

Thus, the survivin proteins of the present invention include molecules having the amino acid sequences disclosed in Ambrosini et al. (1997); fragments thereof having a consecutive sequence of at least about 3, 5, 10, or 15 or more amino acid residues of the survivin protein; amino acid sequence variants of such sequence wherein an amino acid residue has been inserted N- or C-terminal to, or within, the survivin sequence; amino acid sequence variants of the survivin sequence, or their fragments as defined above, that have been substituted by another residue. Contemplated variants further include those containing predetermined mutations by, e.g., homologous recombination, site-directed or PCR mutagenesis, the corresponding survivin proteins of other animal species, including but not limited to rabbit, rat, murine, porcine, bovine, ovine, equine and non-human primate species, the alleles or other naturally occurring variants of the survivin family of proteins; and derivatives wherein the survivin protein has been covalently modified by substitution, chemical, enzymatic, or other appropriate means with a moiety other than a naturally occurring amino acid (for example a detectable moiety such as an enzyme or radioisotope). The recombinant survivin protein also can be used to solve the molecular structure of survivin by 2D-NMR, circular dichroism and X-ray crystallography, thus integrating the site-directed mutagenesis approach and the rational design of specific small molecule inhibitors.

As used herein, the term "caspase-9" includes any caspase-9 protein that interacts with phosphorylated survivin. The term includes the activated form of the caspase-9, naturally occurring allelic variants of caspase-9, naturally occurring caspase-9 proteins isolated from different sources, variants of caspase-9 that interact with survivin, and fragments of caspase-9 that interact with survivin. As used herein, pro-caspase-9 refers to the proform of caspase-9 (see Zou, H. et al., 1999).

As used herein, the term "$p34^{cdc2}$-cyclin B1 kinase complex" refers to a complex comprising $p34^{cdc2}$ and cyclin B1 kinase. The term "$p34^{cdc2}$" includes any $p34^{cdc2}$ protein that forms a complex with cyclin B1 and the resulting complex phosphorylates and binds survivin. The term includes naturally occurring allelic variants of $p34^{cdc2}$, naturally occurring $p34^{cdc2}$ proteins isolated from different sources, variants of $p34^{cdc2}$ that interact with survivin, and fragments of $p34^{cdc2}$ that interact with survivin. The term "cyclin B1" includes any cyclin B1 protein that forms a complex with $p34^{cdc2}$ and the resulting complex phosphorylates and binds survivin. The term includes naturally occurring allelic variants of cyclin B1, naturally occurring cyclin B1 proteins isolated from different sources, variants of cyclin B1 that interact with survivin, and fragments of cyclin B1 that interact with survivin.

Assays of the invention may be modified or prepared in any available format, including high-throughput assays that monitor the binding of survivin and p34$^{cdc2}$-cyclin B1 kinase complex or the binding of survivin to caspase-9. In many drug screening programs which test libraries of compounds, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an inhibition of, for instance, binding between two molecules.

In one embodiment of a high-throughput screening assay survivin, p34$^{cdc2}$-cyclin B1 kinase complex, and caspase-9 may be added to the wells of a microtiter plate in the presence and absence of the agents to be tested. Caspase-9 substrates that are commercially available could be included in the wells and the cleavage or release of the substrate can be assayed using continuous-reading instruments as described in Quan et al. (1995) *J. Biol. Chem.* 270:10377-10379 or Stennicke et al. (1997) *J. Biol. Chem.* 272: 25719-25723.

In another embodiment of a high-throughput screening assay, the assay can be formulated to detect the ability of a test compound to inhibit binding, competitive or non-competitive, of survivin to the p34$^{cdc2}$-cyclin B1 kinase complex or of survivin to caspase-9. The inhibition of complex formation may be detected by a variety of techniques. For instance, modulation of the formation of complexes can be quantitated using, for example, detectably labeled survivin such as radiolabeled (e.g. $^{32}$P, $^{35}$S, $^{14}$C or $^{3}$H), fluorescently labeled (e.g. FITC), or enzymatically labeled survivin, by immunoassay, or by chromatographic detection.

To illustrate, there are a variety of binding assays known in the art for detecting H2-receptor antagonists based on their ability to inhibit binding of known H2 receptor ligands (including other antagonists). In one embodiment, the in vitro assay described by Norris et al. ((1985) *Agents Actions* 16:170) can be used to score for substituted N-heteroaromatics which bind to the H2-receptor (and which may be further characterized in subsequent biological assays as agonists or antagonists of that receptor). In particular, the Norris et al. assay utilizes a competitive binding assay which detects inhibition of $^{3}$H-tiotidine binding to guinea-pig cerebral cortex H2 receptors.

In certain assays, the receptor, subunits thereof, or even the other target protein to which binding is to be assessed, can be provided in a pure or semi-pure form. Typically, for those instances, it will be desirable to immobilize one of the proteins to facilitate separation of protein-protein complexes from uncomplexed forms, as well as to accommodate automation of the assay. Binding of one protein to a second protein, for instance binding of survivin to p34$^{cdc2}$-cyclin B1 kinase complex or binding of survivin to caspase-9, in the presence and absence of a candidate agent, can be accomplished in any vessel suitable for containing the reactants. Examples include microtitre plates, test tubes, and microcentrifuge tubes. In one embodiment, a fusion protein can be provided which adds a domain that allows the protein to be bound to a matrix. For example, glutathione-S-transferase (GST) fusion proteins can be adsorbed onto glutathione sepharose beads (Sigma Chemical, St. Louis, Mo.) or glutathione derivatized microtitre plates, which are then combined with the remaining labeled protein (ligand) and the test compound. The mixture is then incubated under conditions conducive to complex formation. Following incubation, the beads are washed to remove any unbound ligand, and the matrix immobilized label determined directly, or in the supernatant after the protein/ligand complexes are subsequently dissociated. When amenable, the complexes can be dissociated from the matrix, separated by SDS-PAGE, and the level of ligand found in the bead fraction quantitated from the gel using standard electrophoretic techniques.

Other techniques for immobilizing proteins on matrices are also available for use in the subject assay. For instance, either protein can be immobilized utilizing conjugation of biotin and streptavidin. Biotinylated molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the protein but which do not interfere with ligand binding can be derivatized to the wells of the plate, and the first protein, such as polymerized tubulin, trapped in the wells by antibody conjugation. As above, preparations of a ligand and a test compound are incubated in the protein-presenting wells of the plate, and the amount of protein/ligand complex trapped in the well can be quantitated. Exemplary methods for detecting such complexes, in addition to those described above, include immunodetection of complexes using antibodies reactive with the ligand, or which are reactive with the protein and compete for binding with the ligand.

Assays of the invention may also include any available in vivo based screening system to detect the interactions between two proteins. For instance, commonly available genetic systems are capable of rapidly detecting which proteins interact with a known protein, determining which domains of the proteins interact and identifying agents which modulate the interaction between two proteins. One such system is the yeast two-hybrid system wherein two proteins are expressed in yeast: one protein of interest fused to a DNA-binding domain and the other protein of interest fused to a transcriptional activation domain (Fields et al. (1989) *Nature* 340:245; Gyuris et al. (1993) *Cell* 75:791; Harper et al. (1993) *Cell* 75:805; Serrano et al. (1993) *Nature* 366:704; and Hannon et al. (1993) *Genes & Dev.* 7:2378).

The amount of phosphorylated survivin can be quantitated by methods routinely practiced by the skilled artisan. One well-known method employs radiolabeling, electrophoresis, and scintillation counting. After electrophoresis of the phosphorylated samples on SDS-PAGE, the gel is autoradiographed and gel bands containing phosphorylated survivin are excised and placed in a scintillation counter for determining the amount of phosphorylation (U.S. Pat. No. 6,028,171). Alternatively, the phosphorylated samples are precipitated with TCA and counted in a scintillation counter (U.S. Pat. No. 6,028,171). A second well-known method uses an antibody that recognizes phosphorylated compounds. Example 1 discloses an example of an antibody that binds specifically to survivin phosphorylated at Thr34. The antibody does not recognize unphosphorylated survivin. An antibody can be used to directly immunoprecipitate phosphorylated survivin from a sample. After immunoprecipitation, the sample can be counted in a scintillation counter. Also, immunoprecipitation with survivin antibody followed by electrophoresis of immunoprecipitated sample, gel transfer onto nitrocellulose, and immunoblot with an antibody is another method of using anti-phosphotyrosine antibody to quantitate the amount of phosphorylated compound (U.S. Pat. No. 5,635,388). Moreover, the amount of phosphorylated survivin can be determined by quantitative densitometry. Recently, Angeles et al. developed a new method of quantitating phosphorylation using an anti-phosphotyrosine antibody with a colorimetric readout or a lanthanide (europium)-labeled anti-phosphotyrosine antibody with a fluorometric detection (Angeles et al., Anal Biochem (2000), 278(2):93). Further, quantitation of phosphorylated survivin can be performed using microtiter plates.

Kinase assays are useful as tools for in vitro detection of agents that modulate the binding of survivin and $p34^{cdc2}$-cyclin B1 kinase or survivin and caspase-9. The amount of phosphorylated survivin in the presence and absence of the agent would enable the skilled artisan to determine whether the agent inhibits binding of survivin and $p34^{cdc2}$-cyclin B1 kinase or survivin and caspase-9.

The above assays may be modified to screen for agents that dephosphorylate survivin at Thr34. These agents would be expected to act as potential tumor suppressors, removing survivin phosphorylation and preventing the formation of the anti-apoptotic complex with caspase. The assay can be performed by modifying a standard in vitro kinase assay to detect or quantitate the amount of dephosphorylated survivin in the presence of the agent and compared to that in the absence of the agent. Potential libraries could be screened for proteins that dephosphorylate survivin.

B. Apoptosis Assays

As a second step in the identification of agents which modulate phosphorylation of survivin, the interaction between survivin and $p34^{cdc2}$-cyclin B1 kinase complex, or the interaction between survivin and caspase-9, agents identified by the primary screen may then be evaluated in an apoptosis assay to determine the apoptotic activity of the agent. Specific examples of apoptosis assays are widely available in the art as exemplified in the following references. Assays for apoptosis in lymphocytes are disclosed by: Li et al., (1995) *Science* 268:429-431; Gibellini et al. (1995) *Br. J. Haematol.* 89:24-33; Martin et al. (1994) *J. Immunol.* 152:330-42; Terai et al., (1991) *J. Clin Invest.* 87:1710-5; Dhein et al. (1995) *Nature* 373:438-441; Katsikis et al. (1995) *J. Exp. Med.* 1815:2029-2036; Westendorp et al. (1995) *Nature* 375:497; and DeRossi et al. (1994) *Virology* 198:234-44.

Assays for apoptosis in fibroblasts are disclosed by: Vossbeck et al. (1995) *Int. J. Cancer* 61:92-97; Goruppi et al. (1994) *Oncogene* 9:1537-44; Fernandez et al. (1994) *Oncogene* 9:2009-17; Harrington et al. (1994) *EMBO J.*, 13:3286-3295; and Itoh et al., (1993) *J. Biol. Chem.* 268:10932-7.

Assays for apoptosis in neuronal cells are disclosed by: Melino et al. (1994) *Mol. Cell Biol.* 14:6584-6596; Rosenblaum et al. (1994) *Ann. Neurol.* 36:864-870; Sato et al. (1994) *J. Neurobiol.* 25:1227-1234; Ferrari et al. (1995) *J. Neurosci.* 1516:2857-2866; Talley et al. (1995) *Mol. Cell Biol.* 1585:2359-2366; Talley et al. (1995) *Mol. Cell. Biol.* 15:2359-2366; and Walkinshaw et al. (1995) *J. Clin. Invest.* 95:2458-2464.

Assays for apoptosis in insect cells are disclosed by: Clem et al. (1991) *Science* 254:1388-90; Crook et al. (1993) *J. Virol:* 67:2168-74; Rabizadeh et al. (1993) *J. Neurochem.* 61:2318-21; Birnbaum et al. (1994) *J. Virol.* 68:2521-8, 1994; and Clem et al. (1994) *Mol. Cell. Biol.* 14:5212-5222.

C. Uses for Agents that Block the Association of Survivin with $p34^{cdc2}$-Cyclin B1 Kinase Complex As provided in the Background section, survivin inhibits cellular apoptosis. Agents that reduce or block the phosphorylation of survivin, the interaction of survivin with $p34^{cdc2}$-cyclin B1 kinase complex, or the interaction of survivin to caspase-9 can be used to modulate biological and pathologic processes associated with survivin function and activity.

In detail, a biological or pathological process mediated by survivin can be modulated by administering to a subject an agent that blocks the interaction of survivin with $p34^{cdc2}$-cyclin B1 kinase complex, the phosphorylation of survivin, or the interaction of survivin and caspase-9.

As used herein, a subject can be any mammal, so long as the mammal is in need of modulation of a pathological or biological process mediated by survivin. The term "mammal" is meant an individual belonging to the class Mammalia. The invention is particularly useful in the treatment of human subjects.

As used herein, a biological or pathological process mediated by phosphorylation survivin, survivin/$p34^{cdc2}$-cyclin B1 kinase complex, or survivin/caspase-9 interaction of a cell refers to the wide variety of cellular events mediated by survivin. Pathological processes refer to a category of biological processes which produce a deleterious effect. For example, a pathological process mediated by survivin is the inhibition of cellular apoptosis in tumor cells. This pathological process can be modulated using agents that reduce or block survivin phosphorylation, survivin/$p34^{cdc2}$-cyclin B1 kinase complex binding, or survivin/caspase-9 binding.

As used herein, an agent is said to modulate a pathological process when the agent reduces the degree or severity of the process. For example, an agent is said to modulate tumor cell proliferation when the agent decreases the rate or extent of cell division.

D. Methods of Inhibiting the Growth of Tumors Using Survivin Antagonists

As used herein, the term "survivin antagonist" encompasses any compound that antagonizes the expression of survivin or the activity of survivin. Examples of survivin antagonists include survivin mutants, survivin antibodies, survivin antisense nucleic acids, and any compound that will antagonize or inhibit the activity or the expression of survivin. Specific examples of survivin antagonists include but are not limited to dominant-negative survivin mutant Thr$^{34}$→Ala and survivin antisense nucleic acid having a specific sequence.

An antisense survivin molecule is complementary to and capable of hybridizing with the RNA encoded by a survivin gene (the "sense gene"). An antisense survivin molecule is used to inhibit the expression of the survivin gene thereby inhibiting tumor growth and preventing and treating diseases associated with tumor growth.

Antisense nucleic acids are preferably constructed by inverting the coding region of the sense gene relative to its normal presentation for transcription to allow for transcription of its complement, hence the complementariness of the respective RNAs encoded by these DNA's. In order to block the production of mRNA produced by the sense gene, the antisense DNA should preferably be expressed at approximately the same time as the sense gene if the antisense nucleic acid is to be expressed in the cell. The timing must be approximate in the sense that the antisense RNA must be present within the cell to block the function of the RNA encoded by the sense gene. To accomplish this result, the coding region of the antisense DNA is often placed under the control of the same promoter as found in the sense gene thereby causing both to be transcribed at the same time.

For reviews of the design considerations and use of antisense oligonucleotides, see Uhlmann et al. (1990) and Milligan et al. (1993), the disclosures of which are hereby incorporated by reference.

While in principle, antisense nucleic acids having a sequence complementary to any region of the survivin gene may be useful in the tumor growth inhibition methods of the present invention, nucleic acid molecules complementary to a portion of the survivin mRNA transcript including the translation initiation codon are particularly preferred. Also preferred are nucleic acid molecules complementary to a portion of the survivin mRNA transcript lying within about 40 nucleotides upstream (the 5' direction) or about 40 nucleotides downstream (the 3' direction) from the translation initiation codon.

In another embodiment, antisense oligonucleotides which hybridize or anneal to at least a portion of the survivin mRNA in a cell may be used in the methods of the invention. Such oligonucleotides are typically short in length and fairly easily diffusible into a cell. Such antisense oligonucleotides include, but are not limited to, polydeoxynucleotides containing 2'-deoxy-D-ribose, polyribonucleotides containing D-ribose, any other type of polynucleotide which is an N-glycoside of a purine or pyrimidine base, or other polymers containing nonnucleotide backbones (e.g., protein nucleic acids and synthetic sequence specific nucleic acid polymers commercially available) or nonstandard linkages, providing that the polymers contain nucleotides in a configuration which allows for base pairing and base stacking such as is found in DNA and RNA. They may include double- and single-stranded DNA, as well as double- and single-stranded RNA and DNA:RNA hybrids, and also include, as well as unmodified forms of the polynucleotide or oligonucleotide, known types of modifications, for example, labels which are known to those skilled in the art, "caps", methylation, substitution of one or more of the naturally occurring nucleotides with analogue, internucleotide modifications such as, for example, those with uncharged linkages (e.g., methyl phosphonates, phosphorotriesters, phosphoramidates, carbamates, etc.) and with charged linkages or sulfur-containing linkages (e.g., phosphorothioates, phosphorodithioates, etc.), those containing pendant moieties, such as, for example, proteins (including nucleases, nuclease inhibitors, toxins, antibodies, signal peptides, poly-L-lysine, etc.) and saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., alpha anomeric nucleic acids, etc.).

The terms "nucleoside", "nucleotide" and "nucleic acid" as used concerning survivin antisense nucleic acid molecules, include those moieties which contain not only the known purine and pyrimidine bases, but also other heterocyclic bases which have been modified. Such modifications include methylated purines and pyrimidines, acylated purines and pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

The present invention provides a method of inhibiting tumor growth by administering a survivin antagonist to the site of tumor growth. As shown in the examples, subclones of YUSAC-2 human melanoma cells stably transfected with survivin antagonist, survivin antisense or a dominant-negative survivin mutant ($Thr^{34} \rightarrow Ala$) under the control of a tetracycline (tet)-regulated promoter were generated. Cells expressing these survivin antagonists underwent spontaneous apoptosis in vitro and did not form tumors upon subcutaneous injection into CB.17 mice. Expression of survivin $Thr^{34} \rightarrow Ala$ mutant in established tumors slowed their growth and caused apoptosis and aberrant mitotic progression in melanoma cells. Manipulation of the apoptotic pathway by targeting survivin may be beneficial in cancer therapy. The survivin antagonists of the present invention can be used to treat patients diagnosed with cancer.

E. Administration of Agents that Modulate Survivin/ $p34^{cdc2}$-Cyclin B1 Kinase Complex Interactions and Survivin/Caspase-9 Interactions The agents of the present invention, such as agents that block survivin phosphorylation, survivin/$p34^{cdc2}$-cyclin B1 kinase complex association, or survivin/caspase-9 interaction can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. For example, as a means of blocking survivin inhibition of apoptosis in tumor cells or to inhibit survivin induced angiogenesis, an agent that blocks survivin phosphorylation, survivin/$p34^{cdc2}$-cyclin B1 kinase complex association is administered systemically or locally to the individual being treated. As described below, there are many methods that can readily be adapted to administer such agents.

The present invention further provides compositions containing one or more agents that block phosphorylation of survivin, survivin/$p34^{cdc2}$-cyclin B1 kinase complex association, or survivin/caspase-9 association. While individual needs vary, a determination of optimal ranges of effective amounts of each component in the composition is within the skill of the art. Typical dosages comprise 0.1 to 100 µg/kg body wt. The preferred dosages comprise 0.1 to 10 µg/kg body wt. The most preferred dosages comprise 0.1 to 1 µg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice, such as chemotherapeutic agents.

F. Methods of Delivering a Survivin Antagonists

Survivin antagonists that are not nucleic acid molecules can be delivered to target sites as discussed under Section E, above. Survivin antagonists that are nucleic acid molecules can be delivered to target sites as discussed below.

Gene therapy is a method for delivering functionally active therapeutic or other forms of genes into targeted cells. Initial efforts of gene transfer into somatic tissues have relied on indirect means called ex vivo gene therapy, wherein target cells are removed from the body, transfected or infected with vectors carrying recombinant genes, and re-implanted into the body. Techniques currently used to transfer DNA in vitro into cells include calcium phosphate-DNA precipitation, DEAE-Dextran transfection, electroporation, liposome mediated DNA transfer or transduction with recombinant viral vectors. These transfection protocols have been used to transfer DNA into different cell types including epithelial cells (U.S. Pat. No. 4,868,116; Morgan et al., 1987), endothelial cells (WO89/05345), hepatocytes (Ledley et al., 1987; Wilson et al., 1990) fibroblasts (Rosenberg et al., 1988; U.S. Pat. No. 4,963,489), lymphocytes (U.S. Pat. No. 5,399,346; Blaese et al., 1995) and hematopoietic stem cells (Lim et al., 1989; U.S. Pat. No. 5,399,346).

Direct in vivo gene transfer has been carried out with formulations of DNA trapped in liposomes (Ledley et al., 1987), or in proteoliposomes that contain viral envelope receptor proteins (Nicolau et al., 1983), and with DNA coupled to a polylysine-glycoprotein carrier complex. In addition, "gene guns" have been used for gene delivery into cells (Australian Patent No. 9068389). Lastly, naked DNA, or DNA associated with liposomes, can be formulated in liquid carrier solutions for injection into interstitial spaces for transfer of DNA into cells (WO90/11092).

Viral vectors are often the most efficient gene therapy system, and recombinant replication-defective viral vectors have been used to transduce (i.e., infect) cells both ex vivo and in vivo. Such vectors include retroviral, adenovirus and adeno-associated and herpes viral vectors. Accordingly, in one embodiment the survivin transgene or survivin antisense molecule can be subloned into an appropriate vector and transferred into a cell or tissue by gene transfer techniques discussed above.

In another embodiment, the survivin antisense molecule can be provided to the cell or tissue using a transfection facilitating composition, such as cationic liposomes containing desired polynucleotide.

G. Combination Therapy

Agents and survivin antagonists of the present invention, can be provided alone, or in combination with other agents that modulate a particular biological or pathological process. For example, an agent of the present invention that inhibits survivin/p34$^{cdc2}$-cyclin B1 kinase complex association, survivin phosphorylation, or survivin/caspase-9 interaction can be administered in combination with anti-cancer agents in methods to control cancer cell growth. Likewise, a survivin antagonist can be administered in combination with anti-cancer agents to inhibit growth of tumor. As used herein, two agents are said to be administered in combination when the two agents are administered simultaneously or are administered independently in a fashion such that the agents will act at the same time.

Inhibition of survivin activity can be used in combination with conventional chemotherapies or anti-angiogenesis agents. The timing for using such agents in combination with agents that inhibit survivin activity depends upon the chemotherapeutic agent used and the tumor cell type treated. Examples of chemotherapeutic agents that can be used in combination with agents that effect survivin activity, include, but are not limited to alkylating agents, such as cyclophosphamide (CTX; cytoxan), chlorambucil (CHL; leukeran), cisplatin (CisP; platinol) busulfan (myleran), melphalan, carmustine (BCNU), streptozotocin, triethylenemelamine (TEM), mitomycin C, and the like alkylating agents; antimetabolites, such as methotrexate (MTX), etoposide (VP16; vepesid) 6-mercaptopurine (6 MP), 6-thioguanine (6TG), cytarabine (Ara-C), 5-fluorouracil (5FU), dacarbazine (DTIC), and the like anti-metabolites; antibiotics, such as actinomycin D, doxorubicin (DXR; adriamycin), daunorubicin (daunomycin), bleomycin, mithramycin and the like antibiotics; alkaloids, such as vinca alkaloids such as vincristine (VCR), vinblastine, and the like; and other antitumor agents, such as taxol and taxol derivatives, the cytostatic agents glucocorticoids such as dexamethasone (DEX; decadron) and corticosteroids such as prednisone, nucleoside enzyme inhibitors such as hydroxyurea, amino acid depleting enzymes such as asparaginase, and the like diverse antitumor agents.

The use of the cytotoxic agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using the present histoculture methods. Generally, the dosage will be reduced compared to the amount used in the absence of agents the effect Survivin activity/expression.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. All articles, publications, patents and documents referred to throughout this application are hereby incorporated by reference in their entirety.

EXAMPLES

Materials and Methods

Cell lines. Cervical carcinoma HeLa cells (American Type Culture Collection) were maintained in Dulbecco's modified minimal Eagle's medium (DMEM; GIBCO BRL, Grand Island, N.Y.) medium, containing 10% fetal calf serum (FCS, Gemini Bio-Products, Calabasas, Calif.), and antibiotics. The YUSAC-2 melanoma cell line expressing endogenous survivin was characterized previously (Grossman et al., 1999). Cell-cycle synchronization was carried out as described (Li et al., 1998), by culture in the presence of 400 µM mimosine (G1), 2 mM thymidine (S) or 0.4 µg/ml nocodazole (G2/M), for 16-h at 37 C. Cell cycle arrest under the various conditions was confirmed by DNA content analysis by propidium iodide staining and flow cytometry.

Antibodies. An affinity-purified rabbit antibody to wild type recombinant survivin was described previously (Grossman et al., 1999). Anti-survivin mAb 8E2 (IgG1) was used in immunofluorescence, as described (Li et al., 1998). Rabbit antibodies to caspase-9 (1:2000 dilution) and caspase-8 (1 µg/ml) were purchased from Pharmingen, San Diego, Calif. Rabbit antibodies to p34$^{cdc2}$ (1-10 µg/ml) and Cdk2 (10 µg/ml) were purchased from Zymed, San Francisco, Calif., and Santa Cruz, respectively. A rat antibody to HA (0.1-5 µg/ml) was from Boehringer Mannheim, San Diego, Calif. A rabbit antibody was raised against the survivin peptide sequence L$^{28}$EGCACT*PERMAEAGFI$^{44}$ (SEQ ID NO; 1) containing phosphorylated Thr$^{34}$(*), according to published protocols (Grossman et al., 1999). Aliquots of the immune serum were precleared by overnight incubation with Sepharose 2B under constant agitation at 4° C., applied to a Sepharose column containing the parent non-phosphorylated survivin peptide L$^{28}$ EGCACTPERMAEAGFI$^{44}$ (SEQ ID NO: 1), and unbound material was further affinity purified on a phosphorylated L$^{28}$EGCACT*PERMAEAGFI$^{44}$ (SEQ ID NO: 1) survivin peptide column. Bound immunoglobulins were eluted in 0.1 M glycine, pH 2.5, neutralized, dialyzed overnight against PBS, pH 7.4, and used in immunoblotting experiments at 10 µg/ml. Antibodies that recognize phosphorylated survivin can be used in the methods of the invention and may also be used to monitor the efficacy of treatment with an antagonist of survivin phosphorylation or may be used to detect phosphorylated survivin in cell samples, such as tumor samples by immunohistochemistry or Western blot.

Oligonucleotides, plasmids and recombinant proteins. Site-directed mutagenesis of the wild type survivin cDNA (Ambrosini et al., 1997) was carried out using the GeneEditor system (Promega, Madison, Wis.), with the targeting oligonucleotide 5'GGCTGCGCCTGCgCCCCGGAGCGGATG3' (SEQ ID NO: 2) to insert the Thr$^{34}$ÕAla (T34A) substitution, according to the manufacturer's specifications. After antibiotic selection, the mutated plasmid DNA was isolated, and confirmed by DNA sequencing. A survivin(T34A) cDNA was also separately inserted in the HindIII/EcoRI sites of pcDNA3 (Invitrogen, San Diego, Calif.) and pEGFPc1 (Clontech, San Francisco, Calif.) vectors. HA-tagged constructs encoding wild type survivin and survivin(T34A) were obtained by PCR using a 5'-oligonucleotide 5'CCCAAGCT-TATGTATCCGTATGATGTTCCTGATTAT-GCTGGTGCCCCGACGT TGCCC3' (SEQ ID NO: 3) containing the HA tag and a 3'-oligonucleotide 5'CGGGATCCGGAAGTGGTGCAGCCACTCTG3' (SEQ ID NO: 4, wild type survivin) or 5'ACGAATTCAATC-CATGGCAGCCAG3' (SEQ ID NO: 5, survivin(T34A)). PCR products were digested with either HindIII/BamHI (522 bp, HA-survivin), or HindIII/EcoRI (473 bp, HA-survivin (T34)), directionally cloned in pcDNA3, and confirmed by DNA sequencing. A wild type survivin cDNA in pEGFPc1 was characterized previously (Li et al., 1999).

A caspase-9 cDNA encoding Met$^1$-Asp$^{330}$ was amplified by PCR with oligonucleotides 5' (5'CCCAAGCTTCCATG-GACGAAGCGGATCGG3', forward, SEQ ID NO: 6) and (5'CGGAATTCTTAGTCCAGCTGGTCGAAGGTC3', reverse, SEQ ID NO: 7), digested with HindIII/EcoRI, directionally cloned in pEGFPc1, and confirmed by DNA sequencing. A caspase 9 dominant negative mutant (Cys$^{287}$ÕAla) was generated by overlapping PCR by amplifying a 5' product of the caspase-9 cDNA of 892 nt with oligonucleotides 5'CCCAAGCTTCCATGGACGAAGCGGATCGG3' (forward, SEQ ID NO: 6) and 5'GTCTTTCTGCTCCCCAC-CggcGGCCTGGATGAAAAAGAGC3' (reverse, SEQ ID NO: 8), and a 3' product of 422 nt with oligonucleotides 5'GCTCTTTTTCATCCAGGCCgccGGTGGG-GAGCAGAAAGAC3' (forward, SEQ ID NO: 9) and 5'CGGAATTCTTATGATGTTTTAAA-GAAAAGTTTTTTCC3' (reverse, SEQ ID NO: 10). Equal concentrations of each gel-purified caspase 9 fragment were amplified by PCR using oligonucleotides 5'CCCAAGCTTC-CATGGACGAAGCGGATCGG3' (forward, SEQ ID NO: 6) and 5'CGGAATTCTTATGATGTTTTAAA-GAAAAGTTTTTTCC3' (reverse, SEQ ID NO: 10). The resulting product of 1272 nt PCR was digested with HindIII/EcoRI, directionally cloned in pcDNA3 or pEGFPc1 and confirmed by DNA sequencing. All plasmids were purified by ion-exchange chromatography (Qiagen, Valencia, Calif.). Wild type survivin or survivin(T34A) in pGEX2T (Pharmacia, Piscataway, N.J.) were expressed as GST fusion proteins in BL21 E. Coli as described previously (Li et al., 1998). The recombinant proteins were released from the GST frame by overnight cleavage with thrombin followed by neutralization in 1-M benzamidine and overnight dialysis in PBS, pH 7.4. A caspase-8(C360S) dominant negative mutant (Boldin et al., 1996) was obtained from Dr. V. Dixit (Genentech Inc. San Francisco).

Transfection experiments. For transient transfection, HeLa cells in C-6 tissue culture plates (Costar, Cambridge, Mass.) at ~60-70% confluency, were incubated in 1 ml of serum-free OptiMEM medium (Life Technologies, Gaithersburg, Md.) for 20 min, and transfected with 2.5 µg of the various plasmid cDNAs plus 9 µl Lipofectamine (Life Technologies). After a 5 h incubation at 37° C., the mixture was aspirated and substituted with complete growth medium for 48-72 h. To generate stable YUSAC-2 transfectants, a survivin(T34A) cDNA was inserted into the HindIII-SpeI sites of the pTet-splice vector (Dr. D. Schatz, Yale University School of Medicine), downstream of the regulatory sequences of the Tet-resistance operon (TetO). YUSAC-2 cells were transfected with 0.8 µg pTet-T34A, 0.8 µg of the transactivation/selection plasmid ptTA-Neo and 5 µl Lipofectamine in 1 ml of OptiMem. Forty-eight h after transfection, cells were re-plated at low density in 15×150 mm plates in growth medium containing 1.5 mg/ml Geneticin (G418, Life Technologies), 2 mM sodium hydroxide and 0.5 µg/ml Tet (Sigma, St. Louis, Mo.) (selection medium). After a 3-week culture, ninety-six individual clones were screened for differential growth in the presence or absence of Tet. Three clones exhibited no growth in the absence of Tet, and one of them (F5.C4) was re-cloned by limiting dilution.

Flow cytometry. HeLa cells transfected with the various GFP constructs in the presence or in the absence of the broad-spectrum caspase inhibitor Z-VAD-fmk (20 µM) were harvested after 48-h (non-adherent and adherent cells), washed in PBS, pH 7.0, and fixed in cold 70% ethanol for 30 min on ice. After washes in PBS, cells ($10 \times 10^6$/ml) were stained with 25 µg/ml propidium iodide (Sigma), 0.05% Triton X-100 and 100 µg/ml RNAse A (Boehringer Mannheim, Indianapolis, Ind.) for 45 min at 22° C. Gated GFP-expressing cells were analyzed for DNA content by flow cytometry on a FACSort (Becton Dickinson, San Jose, Calif.) using a Cell Quest software. In other experiments, F5-C4 cells were synchronized at the G1/S boundary by culture with 5-mM thymidine for 16 h at 37° C., in the presence or in the absence of Tet. At the end of the incubation, cells were released from the thymidine block, and harvested at 3-h intervals for DNA content analysis by propidium iodide staining and flow cytometry, or, alternatively, for caspase-9 processing by Western blotting (see below).

TUNEL staining. Internucleosomal DNA fragmentation of F5.C4 cells in the presence or in the absence of Tet was carried out by end-labeling with terminal deoxynucleotidyl transferase (TdT) and peroxidase-conjugated anti-digoxigenin antibody using the ApopTag kit (Intergen, Purchase, N.Y.), as described previously (Grossman et al., 1999).

Immunoprecipitation and Western blotting. Asynchronously growing or synchronized HeLa cells were lysed in 200 µl of lysis buffer containing 50 mM Tris, pH 7.5, 1% NP-40, 0.25% DOC, 150 mM NaCl, 1 mM PMSF, 10 µg/ml aprotinin, 10 µg/ml leupeptin, 10 µg/ml pepstatin, 1 mM $Na_3VO_4$, 20 mM NaF, 0.2 mM EGTA, 1 mM EDTA, pH 8.0, for 30 min at 4° C. Insoluble material was removed by centrifugation at 14,000 rpm for 15 min, and two-hundred µg of protein lysate was pre-absorbed with 25 µl of a 50:50 Protein A Sepharose slurry (Pharmacia) for 3 h at 4° C. with constant agitation. Precleared lysates were separately incubated with antibodies to $p34^{cdc2}$, Cdk2, or HA for 16 h at 4° C. with constant agitation. The immune complexes were precipitated by addition of 50 µl of a 50:50 Protein A slurry for 2 h at 4° C., washed three times in 350 mM NaCl/lysis buffer, plus three additional washes in 150 mM NaCl/lysis buffer. Samples were separated by electrophoresis on a 12% SDS-polyacrylamide gel, transferred to Immobilon membranes (Millipore Corp.), and separately incubated with antibodies to $p34^{cdc2}$ (µg/ml), caspase-9, caspase-8, survivin, or HA (0.1 µg/ml) in TBS plus Tween-20 for 16 h at 4° C. After washes, the transfer membranes were separately incubated with HRP-conjugated anti-mouse (Amersham), anti-rabbit (Amersham), or anti-rat (Boehringer) secondary antibodies (1:2000), with visualization of immunoreactive bands by chemiluminescence (Amersham). For reprobing, membranes were stripped in 100 mM 2-∃ mercaptoethanol, 2% SDS, 62.5 mM Tris-HCl, pH 6.7, for 30 min at 50° C. In another series of experiments, HeLa cells at 60% confluency were transfected with HA-survivin or HA-survivin(T34A) and replenished with complete growth medium for 8-h at 37° C. Cells were synchronized at the G1/S boundary by treatment with 2 mM thymidine for 16 h at 37° C., released in complete growth medium and harvested at increasing time intervals for immunoprecipitation and DNA content analysis by flow cytometry, as described above.

Survivin phosphorylation and in vitro kinase assays. Exponentially growing HeLa cells were transiently transfected with HA-survivin and allowed to recover for 44 h in complete DMEM. Cells were supplemented with phosphate-free DMEM (Life Technologies) for 1 h at 37° C. Cells were labeled with 200 µCi/ml $^{32}$PI(NEN Life Science Products Inc.) in the presence of 10% phosphate-free serum for an additional 5 h at 37° C. Labeled cells were washed twice in cold PBS, pH 7.4, solubilized in lysis buffer, and immunoprecipitated with an antibody to HA (see above), followed by autoradiography. For in vitro kinase assays, baculovirus-expressed human $p34^{cdc2}$-cyclin B1 or Cdk2-cyclin E kinase complexes were separately incubated with 1 µg histone H1, 6 µg of wild type survivin or survivin(T34A) in a 25 µl reaction mixture containing 20 mM HEPES, pH 7.4, 10 mM $MgCl_2$, 0.5 mM DTT, 10 µM ATP plus 10 µCi of $^{32}$P-ATP (Amersham) for 30 min at 30° C. The reaction was terminated by addition of 25 µl of 2× Laemmli sample buffer. Samples were electrophoresed on a 5-20% SDS polyacrylamide gel, and phosphorylated bands were visualized by autoradiography. Equal protein loading in each kinase reaction was confirmed by Coomassie blue staining of the gel.

Immunofluorescence and confocal microscopy. HeLa cells transfected with the various GFP constructs were harvested after 48 h, and fixed in 4% paraformaldehyde containing 0.25% Triton X-100 for 10 min at 22° C. Cell nuclei were stained with 6.5 µg/ml 4,6-diamidino-2-phenylindole (DAPI, Sigma), 16% polyvinyl alcohol (Air Products and Chemicals, Allentown, Pa.), and 40% glycerol. GFP-expressing cells were independently scored for nuclear morphology of apoptosis (chromatin condensation, DNA fragmentation) using a Zeiss fluorescent microscope, as described (Li et al., 1999). For confocal microscopy analysis, HeLa cells on optical grade glass coverslips were fixed and labeled with mAb 8E2 to survivin or a rabbit antibody to $p34^{cdc2}$, as described (Li et al., 1998). Binding of the primary antibodies was revealed by addition of FITC-labeled goat anti-mouse IgG (survivin) and Texas Red (TR)-conjugated goat anti-rabbit IgG ($p34^{cdc2}$) (Molecular Probes, Junction City, Oreg.). In other experiments, HeLa cells were transfected with HA-survivin, HA-survivin(T34A), or survivin (L64A) and stained with antibodies to HA, mAb 8E2 (L64A), or caspase-9, followed by anti-mouse (FITC) or anti-rabbit (TR)-conjugated antibodies, respectively. For all experiments, non-binding mouse or rabbit IgG were used as controls. Coverslips mounted in Mowiol 4-88 (Hoechst, Frankfurt/Main, Germany) were analyzed on a Zeiss Axiophot microscope or by confocal laser scanning microscopy (CLSM Bio-Rad 1024). Files were assembled and printed with ADOBE Photoshop 5.0.

Example 1

Phosphorylation of Survivin

A. Phosphorylation of Survivin on $Thr^{34}$ by $p34^{cdc2}$-Cyclin B1

Inspection of the primary sequence of survivin revealed a potential phosphorylation site for $p34^{cdc2}$ at $Thr^{34}$ (FIG. 1A).

Figure 1C:
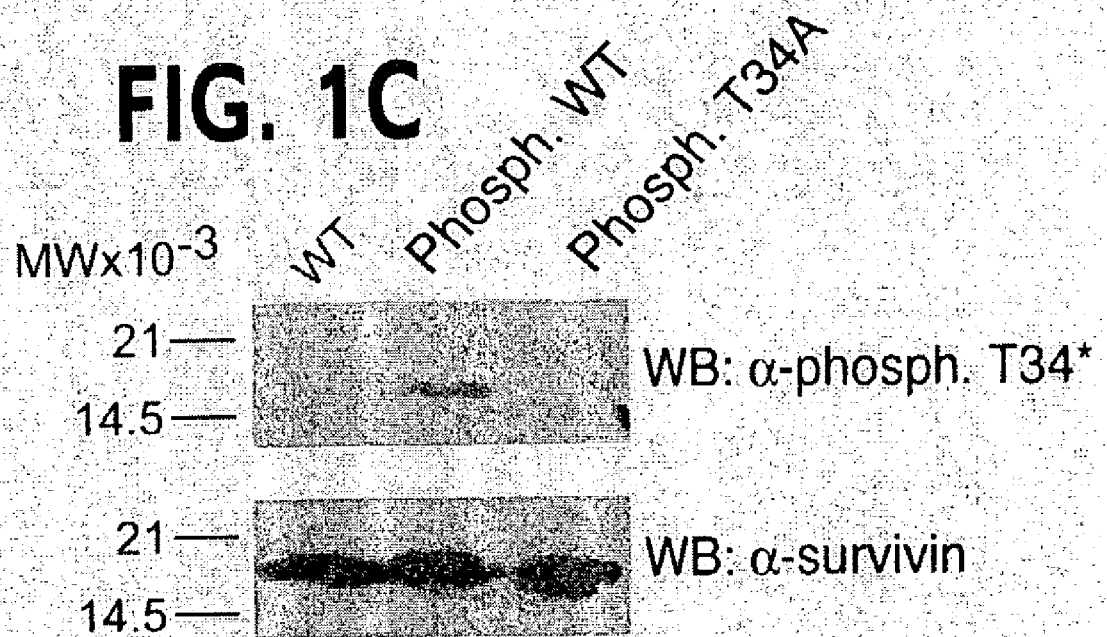
Figure 1D:
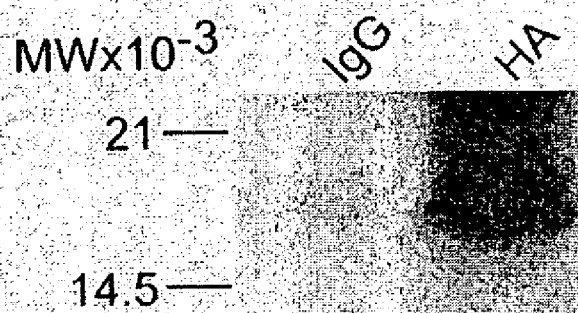

By Clustal alignment, the region $T^{34}$-P-E-R (SEQ ID NO: 11), which matched the p34$^{cdc2}$ consensus phosphorylation sequence S/T-P-X-R (SEQ ID NO: 11) (Holmes and Solomon, 1996), was found only in human and mouse survivin, and was absent in IAP proteins from various species (FIG. 1A and Deveraux and Reed, 1999). In in vitro kinase assays, baculovirus-expressed p34$^{cdc2}$-cyclin B1 readily phosphorylated recombinant wild type survivin, whereas substitution of Thr$^{34}$ÕAla, i.e. survivin(T34A), abolished phosphorylation by p34$^{cdc2}$-cyclin B1 (FIG. 1B). In control experiments, baculovirus-expressed Cdk2-cyclin E did not phosphorylate wild type survivin or survivin(T34A), whereas p34$^{cdc2}$-cyclin B1 or Cdk2-cyclin E readily phosphorylated histone H1 (FIG. 1B). A rabbit antibody was raised against the survivin peptide sequence $L^{28}$EGCACT*PERMAEAGFI$^{44}$ (SEQ ID NO: 1) containing phosphorylated Thr$^{34}$ (T*), sequentially affinity purified on non-phosphorylated/phosphorylated peptide-Sepharose columns and used in immunoblotting. The antibody to phosphorylated Thr$^{34}$ recognized wild type survivin after in vitro phosphorylation by p34$^{cdc2}$-cyclin B1, but not unphosphorylated survivin or survivin(T34A) after incubation with p34$^{cdc2}$-cyclin B1 (FIG. 1C). In contrast, an antibody to survivin (Grossman et al., 1999) indistinguishably recognized wild type survivin or survivin(T34A), with or without p34$^{cdc2}$-cyclin B1-mediated phosphorylation (FIG. 1D). In other experiments, HA-tagged survivin was transfected in HeLa cells metabolically labeled with $^{32}$Pi orthophosphate. Immunoprecipitation with an antibody to HA demonstrated prominent phosphorylation of 16.5 kDa survivin, in vivo, whereas a control non-binding antibody did not immunoprecipitate radiolabeled bands from HeLa cells (FIG. 1D).

B. Physical Association Between Survivin and p34$^{cdc2}$

HeLa cells arrested at G1, S, or G2/M were detergent-solubilized and immunoprecipitated with an antibody to p34$^{cdc2}$. Western blotting of p34$^{cdc2}$ immunoprecipitates from G2/M-arrested HeLa cells revealed the presence of associated 16.5 kDa survivin, which was enriched in mitotic cells as compared with asynchronously growing cultures (FIG. 2A). In contrast, no survivin bands were immunoblotted in p34$^{cdc2}$ immunoprecipitates from G1- or S-arrested cultures (FIG. 2A). Consistent with the specificity of p34$^{cdc2}$ phosphorylation of survivin (FIG. 1), Cdk2 immunoprecipitates from G1-, S-, or G2/M-synchronized HeLa cells did not contain 16.5 kDa survivin by Western blotting (FIG. 2A). In reciprocal experiments, HA-survivin or HA-survivin(T34A) immunoprecipitated from HeLa cells contained a prominent p34$^{cdc2}$ band by Western blotting (FIG. 2B), thus demonstrating that survivin-p34$^{cdc2}$ interaction was independent of Thr$^{34}$. By dual immunofluorescence labeling and confocal microscopy, endogenous p34$^{cdc2}$ and survivin strongly co-localized on mitotic spindle microtubules at prophase and metaphase, and concentrated within midbodies at late telophase (FIG. 2C).

Example 2

Survivin Regulation of Apoptosis

A. Spontaneous Apoptosis Induced by Expression of Non-Phosphorylatable Survivin(T34A)

Figure 3A:
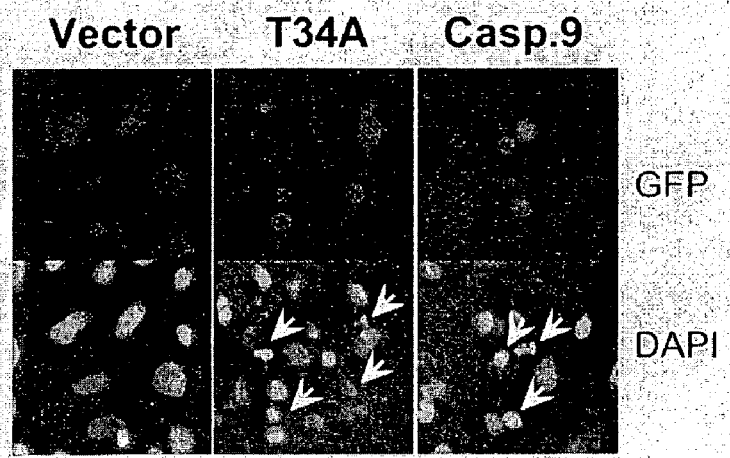
FIGS. 3A-D. Expression of non-phosphorylatable survivin (T34A) induces spontaneous apoptosis and dysregulation of mitosis.
Figure 3B:
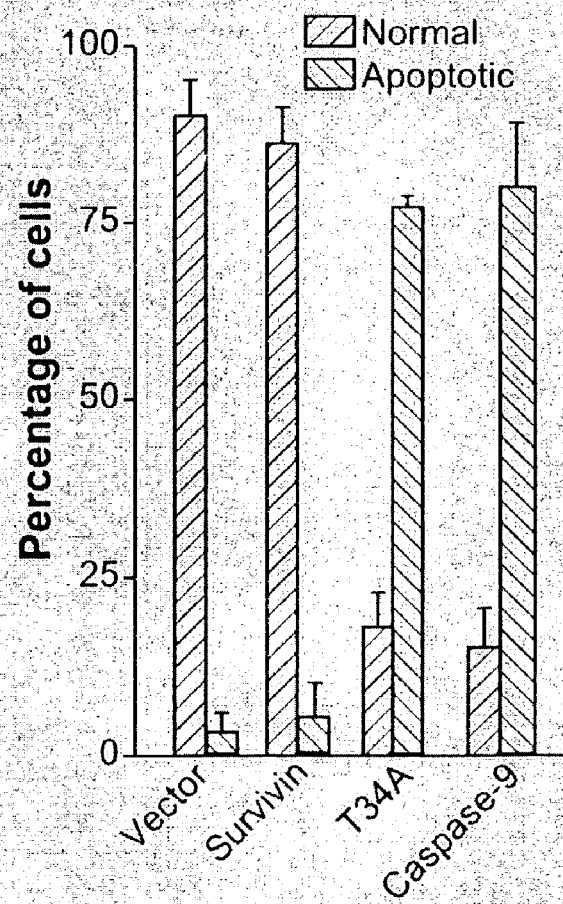
Figure 3C:
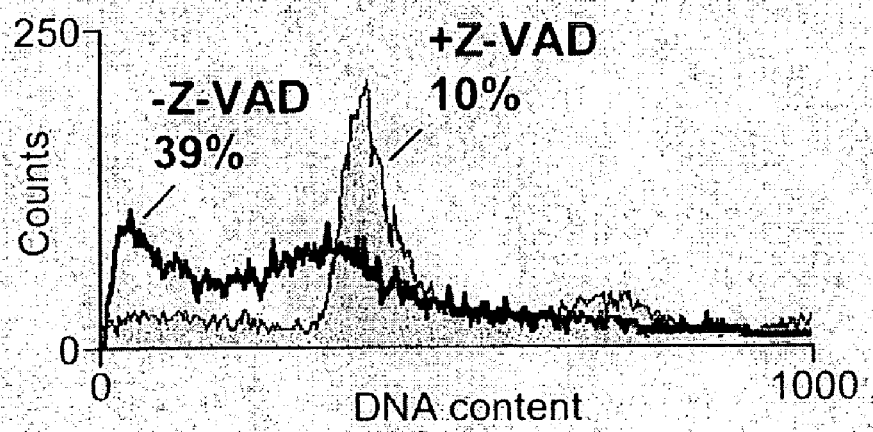
Figure 3D:
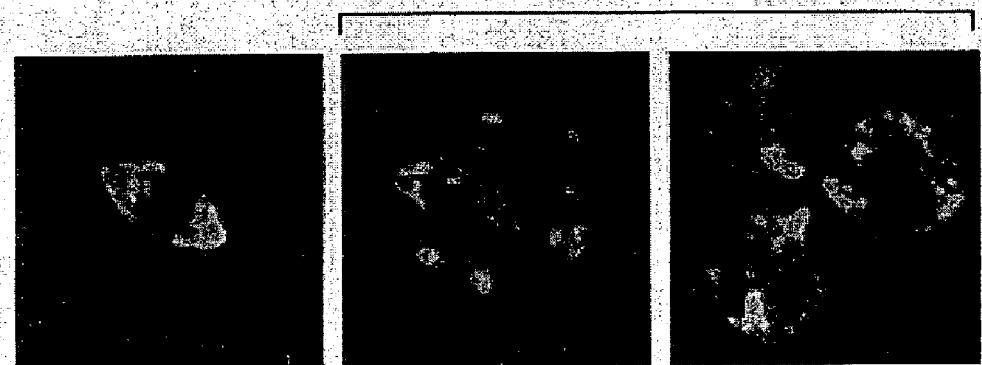

Transfection of HeLa cells with survivin(T34A) fused to a Green Fluorescent Protein (GFP) caused spontaneous chromatin condensation and DNA fragmentation in ~80% of GFP-expressing cells, in the absence of exogenous apoptotic stimuli (FIGS. 3A, B). Similar results were obtained with transfection of GFP-caspase-9 (Met$^1$-Asp$^{330}$), whereas expression of GFP vector or wild type survivin did not affect nuclear morphology in HeLa cells (FIGS. 3A, B). Comparable expression of the various constructs in HeLa cells was confirmed by flow cytometry by gating on the GFP-expressing population (not shown). In other experiments, expression of GFP-survivin(T34A) resulted in the appearance of HeLa cells with hypodiploid (sub-G1) DNA content by propidium iodide staining and flow cytometry, in a reaction reversed by the broad-spectrum caspase inhibitor, Z-VAD-fmk (FIG. 3C). Immunofluorescence labeling of HeLa cells expressing survivin(T34A) with an antibody to 3-tubulin revealed a profound dysregulation of mitotic transitions, characterized by assembly of multipolar and grossly abnormal mitotic spindles (FIG. 3D). In contrast, HeLa cells transfected with wild type survivin formed normal bipolar spindles (FIG. 3D).

Apoptosis Induced by Survivin(T34A) Coincides with Mitosis.

Figure 4A:
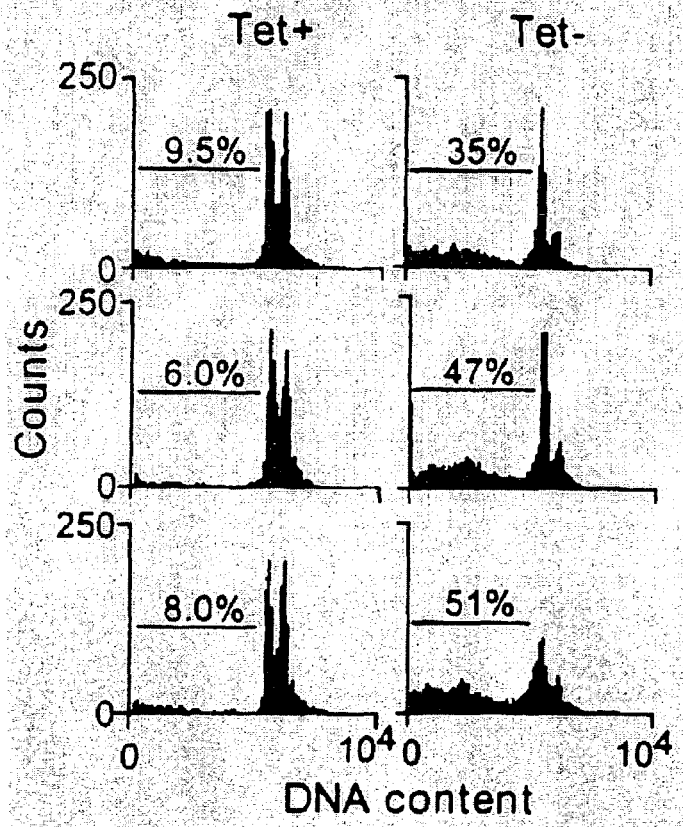
FIGS. 4A-C. Apoptosis induced by survivin(T34A) coincides with mitosis.
Figure 4B:
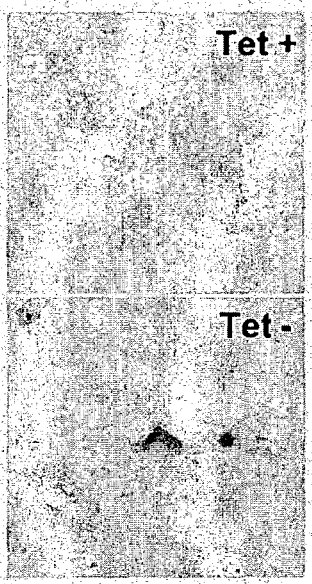

YUSAC-2 melanoma cells expressing endogenous survivin (Grossman et al., 1999) were stably transfected to express survivin(T34A) under the control of a tetracycline (Tet)-regulated promoter (Tet-off system) (Shockett et al., 1995). Withdrawal of Tet from three independent transfected cell lines (Tet−) resulted in strong induction of ~16.5 kDa survivin(T34A) by Western blotting, but not in Tet-containing cultures (Tet+) (not shown). After induction of survivin (T34A), Tet− cell lines exhibited a nearly complete loss of mitotic (G2/M) cells, and appearance of a prominent population with apoptotic (sub-G1) DNA content, by propidium iodide staining and flow cytometry (FIG. 4A). In contrast, Tet+ lines had normal G2/M DNA content and did not exhibit increase in the apoptotic (sub-G1) fraction (FIG. 4A). One transfected YUSAC-2 cell line (F5.C4) was re-cloned by limiting dilution and used in subsequent experiments. Consistent with genuine apoptotic morphology (FIG. 2), F5.C4 cells strongly labeled for internucleosomal DNA fragmentation by TUNEL in the absence, but not in the presence of Tet (FIG. 4B).

Figure 4C:
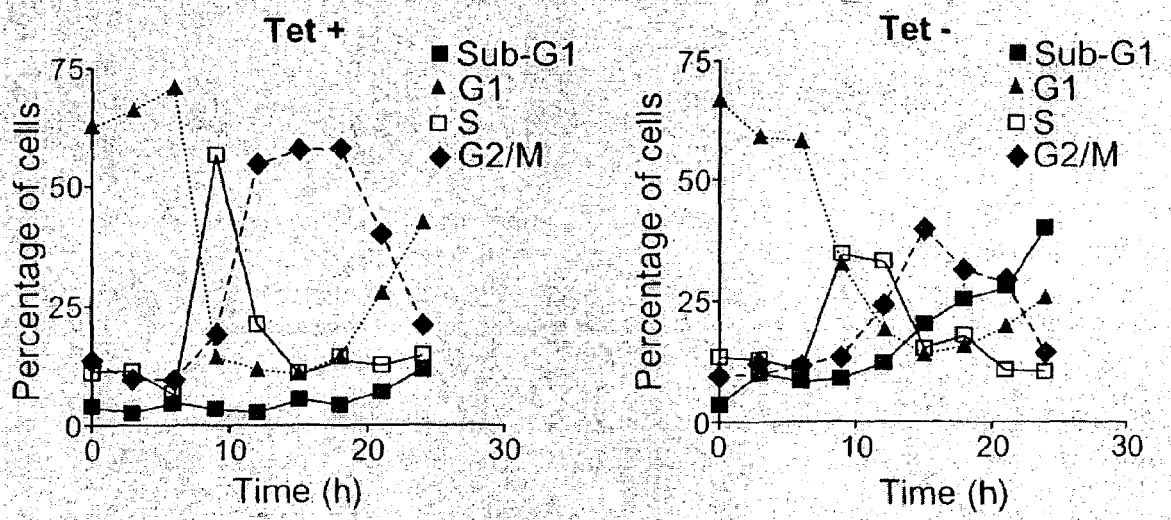

F5.C4 cells were synchronized at the G1/S boundary with or without Tet, released, and monitored for cell cycle transitions at 3-h intervals by propidium iodide staining and flow cytometry. In the presence of Tet (Tet+), F5.C4 cells approached the first mitosis 9 h after thymidine release, completed cell division by 15-18 h, and re-entered G1 after 21 h, without significant changes in the apoptotic (sub-G1) fraction throughout the cell cycle (FIG. 4C). In the absence of Tet, (Tet−) F5.C4 cells exhibited similar kinetics of cell cycle progression (FIG. 4C). However, entry into mitosis of Tet− F5.C4 cells coincided precisely with the appearance of the apoptotic population with sub-G1 DNA content, which increased steadily throughout mitosis and in the post-mitotic phase with considerable reduction of the subsequent G1 peak (FIG. 4C).

Example 3

Survivin and Caspase-9

A. Phosphorylation-Dependent Modulation of Survivin-Caspase-9 Interaction

Figure 5B:
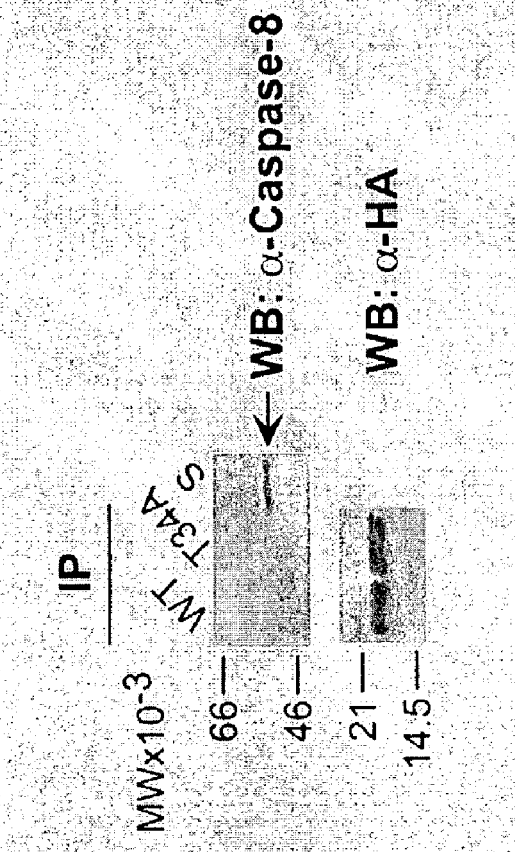
Figure 5A:
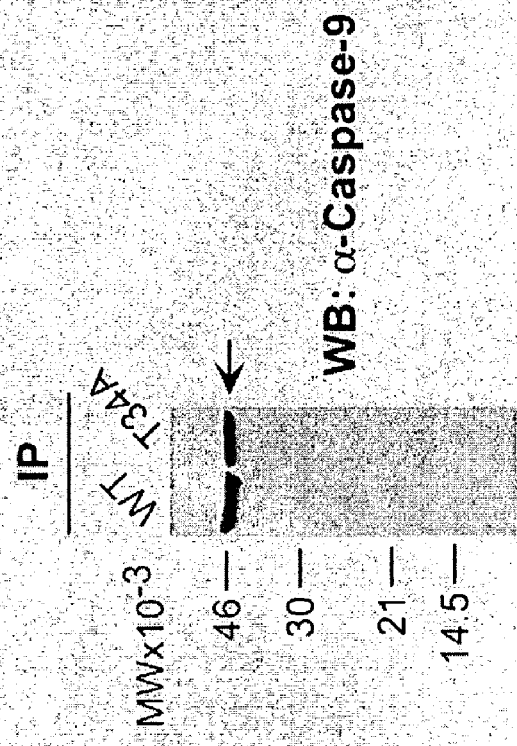

A potential association of survivin with target caspase(s) at mitosis was investigated. Immunoprecipitates of HA-survivin or HA-survivin(T34A) from viable HeLa cells 24 h-after transfection revealed the presence of associated ~46 kDa proform caspase-9, by Western blotting (FIG. 5A). In contrast, immunoprecipitates of wild type survivin or survivin (T34A) did not contain another upstream initiator caspase, caspase-8, by Western blotting (FIG. 5B). Co-immunoprecipitation and Western blotting experiments were repeated from adherent or non-adherent, i.e. mitotic/apoptotic, HeLa cells 48-h after transfection. As shown in FIG. 5C, HA-survivin immunoprecipitates from adherent or non-adherent HeLa cell extracts revealed the presence of associated ~35 kDa active caspase-9, by Western blotting (FIG. 5C). Analysis of the supernatants from these immunoprecipitates revealed a predominant 46 kDa proform caspase-9 band in extracts from adherent cells, and ~35 kDa active caspase-9 in mitotic/apoptotic extracts (FIG. 5C). In contrast, immunoprecipitates of non-phosphorylatable HA-survivin(T34A) from adherent, i.e. viable, HeLa cells contained barely detectable amounts of 35 kDa active caspase-9, and no ~46 kDa proform caspase-9, by Western blotting (FIG. 5C). When similar experiments were repeated using mitotic/apoptotic HeLa cell extracts, immunoprecipitates of HA-survivin(T34A) did not contain associated proform or active caspase-9 bands, by Western blotting (FIG. 5C). Consistent with the data presented above, supernatants from these immunoprecipitates contained ~46 kDa proform caspase-9 in adherent cells, and ~35 kDa active caspase-9 in mitotic/apoptotic extracts (FIG. 5C). To determine if Thr$^{34}$ phosphorylation affected the recognition of survivin for active/proform caspase-9 at mitosis, co-immunoprecipitation and Western blotting experiments were carried out from synchronized HeLa cells during cell cycle progression. Immunoprecipitates of wild type survivin or survivin(T34A) from interphase HeLa cells 0 or 6 h after thymidine release contained proform/active caspase-9 bands of 46 kDa and ~35 kDa, respectively (FIG. 5D). However, in synchronized HeLa cells entering mitosis 12 h after thymidine release, HA-survivin immunoprecipitates became exclusively associated with ~35 kDa active caspase-9, whereas both proform and active caspase-9 bands were detected in the supernatant (FIG. 5D). In contrast, immunoprecipitates of non-phosphorylatable survivin(T34A) from mitotic HeLa cells did not contain associated proform or active caspase-9 bands, which accumulated in the related supernatant (FIG. 5D). In control experiments, entry into mitosis of synchronized HeLa cells 12 h after thymidine release was demonstrated by DNA content analysis and flow cytometry (not shown).

B. Phosphorylation-Dependent Localization of Survivin-Caspase-9 Complex, In Vivo By immunofluorescence and confocal microscopy, HA-survivin and HA-survivin(T34A) transfected in HeLa cells bound to mitotic spindle microtubules at metaphase (not shown), and accumulated in midbodies at telophase, indistinguishably from endogenous survivin (FIGS. 6A, B). In HA-survivin transfectants, simultaneous labeling for caspase-9 revealed a diffuse cytoplasmic reactivity and a prominent co-localization of caspase-9 with survivin in midbodies at different stages of telophase (FIG. 6A), in agreement with the co-immunoprecipitation data presented above. HeLa cells transfected with HA-survivin(T34A) also exhibited a diffuse labeling for caspase-9 throughout the cytoplasm (FIG. 6B). However, in the presence of non-phosphorylatable HA-survivin(T34A), caspase-9 selectively lost its localization to midbodies and did not co-associate with survivin(T34A) at telophase (FIG. 6B), consistent with the dissociation of a survivin(T34A)-active caspase-9 complex (see above). In control experiments, another survivin point mutant in the Baculovirus IAP repeat (BIR), Leu$^{64}$ÖAla, did not cause apoptosis (not shown), and physically co-localized with endogenous caspase-9 in midbodies at telophase (FIG. 6C).

C. Caspase-9-Dependent Apoptotic Checkpoint at Mitosis

To determine if active caspase-9 was responsible for apoptosis induced by non-phosphorylatable survivin(T34A). By Western blotting, apoptosis of cell cycle synchronized Tet–F5.C4 cells was associated with time-dependent cleavage of 46 kDa proform caspase-9 and generation of ~35 kDa and ~37 kDa active caspase-9 bands (FIG. 7A). Consistent with the kinetics of apoptosis of Tet– F5.C4 cells, the generation of active caspase-9 bands began 9-h after thymidine release, increased at mitosis, and peaked in post-mitotic cells 24 h after release, with nearly complete disappearance of the ~46 kDa proform caspase-9 band (FIG. 7A). Indistinguishable results of caspase-9 cleavage were observed in HeLa cells treated with TNFα/cycloheximide (FIG. 7A). In contrast, Tet+F5.C4 cells did not exhibit proteolytic cleavage of ~46 kDa caspase-9 at mitosis (FIG. 7A). In other experiments, transfection of HeLa cells with a caspase-9(C287A) dominant negative mutant (Duan et al., 1996) inhibited nuclear fragmentation and chromatin condensation induced by etoposide (FIG. 7B), in agreement with previous observations (Pan et al., 1998). Expression of caspase-9(C287A) also reversed HeLa cell apoptosis induced by survivin(T34A) to background levels observed in vector control transfectants (FIG. 7B), and restored the co-localization of caspase-9 and endogenous survivin at midbodies (not shown). In control experiments, co-transfection of HeLa cells with a caspase-8 (C360S) dominant negative mutant (Boldin et al., 1996) did not reduce apoptosis induced by survivin(T34A), whereas it completely inhibited cell death induced by TNFα/cycloheximide (FIG. 7B), in agreement with previous observations (Boldin et al., 1996).

The results of Examples 1-3 show that survivin, a IAP apoptosis inhibitor (Deveraux and Reed, 1999) over-expressed in cancer (Ambrosini et al., 1997; Velculescu et al., 1999), physically associates with the cyclin-dependent kinase complex, p34$^{cdc2}$-cyclin B1 (Nurse, 1994), and is phosphorylated by p34$^{cdc2}$ on Thr$^{34}$. Based on the phenotype of cells expressing a non-phosphorylatable survivin(T34A) mutant, phosphorylation on Thr$^{34}$ switches the affinity of survivin for active versus proform caspase-9, and stabilizes this anti-apoptotic complex at mitosis (FIG. 13). Conversely, lack of survivin phosphorylation by p34$^{cdc2}$ causes dissociation of the survivin-active caspase-9 complex, selective mislocalization of caspase-9 from midbodies, and caspase-9-dependent apoptosis of cells traversing mitosis (FIG. 13).

Example 4

Method of Identifying an Agent that Modulates Phosphorylation of Survivin

The interactions described above between survivin and p34$^{cdc2}$-cyclin B1 kinase complex allow for the development of assays to identify an agent which modulates the phosphorylation of survivin. Such assays use, as common steps, a step of contacting survivin and p34$^{cdc2}$-cyclin B1 kinase complex in the presence of the agent and a step of determining whether the agent modulates the phosphorylation of survivin by the kinase complex. Any means to quantitate phosphorylation of survivin may be used.

In one format, the ability of an agent to modulate the phosphorylation of survivin is assayed. Baculovirus-expressed p34$^{cdc2}$-cyclin B1 kinase complexes are incubated with 1 µg histone H1, 6 µg of wild type survivin in the presence and absence of an agent in a 25 µl reaction mixture containing 20 mM HEPES, pH 7.4, 10 mM MgCl$_2$, 0.5 mM DTT, 10 µM ATP plus 10 µCi of $^{32}$P-ATP (Amersham) for 30 min at 30° C. The two reactions are terminated by addition of 25 µl of 2× Laemmli sample buffer. To quantitate the amount of phosphorylated survivin, the above samples are electrophoresed on a 5-20% SDS polyacrylamide gel, and phosphorylated bands are visualized by autoradiography. Equal protein loading in each kinase reaction is confirmed by Coomassie blue staining of the gel. The ability of the agent to modulate phosphorylation of survivin by p34$^{cdc2}$-cyclin B1 kinase complex is then determined by comparing the amount or quantity of phosphorylated survivin in the samples exposed to the agent and the amount or quantity of phosphorylated survivin in the control (non-agent exposed) sample. The amount of phosphorylated survivin is quantitated by cutting the survivin gel bands out and counted in a scintillation counter. The amount of phosphorylated survivin could also be determined by quantitative densitometry.

Example 5

Methods of Identifying an Agent that Modulates Survivin/p34$^{cdc2}$-Cyclin B1 Kinase complex Association or Phosphorylated Survivin/Caspase-9 Complex Association The interactions described above between survivin and p34$^{cdc2}$-cyclin B1 kinase complex and between phosphorylated survivin and caspase-9 allow for the development of assays to identify an agent which modulates survivin and p34$^{cdc2}$-cyclin B1 kinase complex association and survivin and caspase-9 association. Such assays may use, as common steps, a step of contacting survivin and p34$^{cdc2}$-cyclin B1 kinase complex in the presence of the agent and a step of determining whether the agent modulates the binding of survivin with the kinase complex or the binding of survivin with caspase-9.

In one format, the ability of an agent to modulate survivin/p34$^{cdc2}$-cyclin B1 kinase complex association is assayed. Asynchronously growing HeLa cells are transfected with the nucleic acid encoding survivin and detergent-solubilized after 24 h. One sample of detergent solubilized cells is incubated with a test agent. The second sample is not incubated with any test agent. The samples are immunoprecipitated with an antibody to p34$^{cdc2}$, separated by electrophoresis, transferred to nylon membranes and immunoblotted with p34$^{cdc2}$ antibodies. The ability of the agent to modulate survivin/p34$^{cdc2}$-cyclin B1 kinase complex interaction is then determined by comparing the positions of p34$^{cdc2}$-cyclin B1 kinase complex on the gel in the presence and absence of the agent.

Alternatively, agents that modulate survivin/p34$^{cdc2}$-cyclin B1 kinase may be identified by using an in vitro kinase assay, similar to the one described under Example 4. Determining the amount of phosphorylated survivin, by for example, use of the phosphorylated survivin specific antibody described above, and comparing the amount of phosphorylated survivin in the presence and absence of the test agent enables the skilled artisan to determine whether the agent inhibits the phosphorylation of survivin and/or an interaction between survivin and p34$^{cdc2}$-cyclin B1 kinase.

In another format, the ability of an agent to modulate phosphorylated survivin/caspase-9 association is assayed. Baculovirus-expressed p34$^{cdc2}$-cyclin B1 kinase complexes are incubated with 1 µg histone H1, 6 µg of wild type survivin in a 25 µl reaction mixture containing 20 mM HEPES, pH 7.4, 10 mM MgCl$_2$, 0.5 mM DTT, 10 µM ATP plus 10 µCi of $^{32}$P-ATP (Amersham) for 30 min at 30° C. The reaction is terminated. Caspase-9 and a test agent is added to the sample. In the control sample containing baculovirus-expressed p34$^{cdc2}$-cyclin B1 and survivin, only caspase-9 is added. The association between phosphorylated survivin and caspase-9 is then detected. For instance, the samples are immunoprecipitated with an antibody to caspase-9, separated by electrophoresis, transferred to nylon membranes and immunoblotted with caspase-9 antibodies. The ability of the agent to modulate survivin/caspase-9 interaction is then determined by comparing the positions of caspase-9 on the gel in the presence and absence of the agent.

Example 6

The Effect of Survivin Antagonists on Human Melanoma Cells

YUSAC-2 human melanoma cells constitutively expressing endogenous survivin (Grossman et al., 1999b) were stably-transfected with survivin antagonists under the control of a tetracycline (tet)-regulated ("tet-off") promoter system (Shockett et al, 1995).

The Thr$^{34}$→Ala mutation was introduced by site-directed mutagenesis into the 1.6 kb human survivin cDNA (Ambrosini et al., 1997) using the oligonucleotide 5'-GGCT-GCGCCTGCgCCCCGGAGCGGATG-3' (SEQ ID NO: 2) and the GeneEditor system (Promega, The Thr$^{34}$→Ala mutation was introduced by site-directed mutagenesis into the 1.6 kb human survivin cDNA (Ambrosini et al., 1997) using the oligonucleotide 5'-GGCTGCGCCTGCgCCCCGGAGCG-GATG-3' (SEQ ID NO: 2) and the GeneEditor system (Promega, Madison, Wis.) according to the manufacturer's instructions. This mutant was evaluated along with other survivin BIR domain mutants for dominant-negative function by the ability to induce spontaneous apoptosis upon transient transfection into Hela cells, as described (Li et al., 1998), and found to be particularly effective. The survivin cDNA containing the Thr$^{34}$→Ala mutation was cloned into the HindIII-Spe1 sites of pTet-splice (Stratagene, La Jolla, Calif.). To generate the antisense construct, the wild-type survivin cDNA was cloned into pTet-splice in the reverse orientation.

These two survivin antagonists were cloned into pTet-splice downstream of the regulatory sequences of the tet-resistance operon (TetO). The plasmid pTA-Neo, containing the tet-controlled transactivator (tTA) sequence downstream of TetO, and a neomycin resistance gene, was kindly provided by David Schatz (Yale University School of Medicine). In this tandem plasmid system, tet prevents tTA binding to TetO and transcription of the transgene; in the absence of tet, tTA upregulates its own transcription and the transgene is expressed.

YUSAC-2 cells (Grossman et al., 1999) were transfected in 6-well plates by the simultaneous addition of 0.8 µg antagonist vector, 0.8 µg pTA-Neo, 0.5 µg tet (Sigma, St. Louis, Mo.), and 5 µl Lipofectamine (Life Technologies, Gaithersburg, Md.) per well. After 9 hours, the transfection medium was aspirated and replaced with normal medium containing 0.5 µg/ml tet. Forty-eight hours from the start of transfection, cells were trypsinized, washed, and replated at low density in 15×150 mm plates in medium containing 1.5 mg/ml G418

(Life Technologies), 2 mM sodium hydroxide and 0.5 µg/ml tet. This selection medium was changed every six days, and after three weeks 96 colonies were transferred to U-bottom microtiter wells for expansion and screening on the basis of differential growth in the presence and absence of tet. Of the BIR mutant-transfected clones, three did not grow in the absence of tet and two of them (designated F5.C4 and F5.E5) were recloned by limiting dilution. Of the antisense-transfected clones, only one (designated B8) exhibited tet-dependent growth. Cells were maintained in selection medium containing G418 and tet.

Upon withdrawal of tet from the culture medium, YUSAC-2 subclone F5.C4, transfected with the $Thr^{34} \rightarrow Ala$ mutant, strongly expressed a 16.5 kDa induced survivin band by Western blotting (FIG. 8A). By contrast, no modulation of survivin expression was observed when tet was present in the culture medium (FIG. 8A). Another subclone transfected with the $Thr^{34} \rightarrow Ala$ mutant, F5.E5, similarly demonstrated tet-regulated transgene expression (not shown). In subclone B8, transfected with survivin antisense, removal of tet from the medium was associated with rapid expression of survivin antisense RNA as assessed by RT-PCR (not shown). Tet-regulated expression of the $Thr^{34} \rightarrow Ala$ mutant or survivin antisense resulted in a progressive time-dependent loss of mitotic (G2/M) cells and coincident accumulation of apoptotic cells with hypodiploid (sub-G1) DNA content, as assessed by propidium iodide staining and flow cytometry (FIG. 8B, and not shown). Tet-deprived F5.C4 cells exhibited apoptotic nuclear morphology and stained intensely for internucleosomal DNA fragmentation by TUNEL (FIG. 8C). By contrast, F5.C4 cells cultured in the presence of tet demonstrated normal mitotic progression (FIG. 8B) and lack of TUNEL reactivity (FIG. 8C).

Example 7

The Effect of Survivin Antagonists on CB.17 Immunodeficient Mice

To determine whether interference with survivin function by regulated expression of survivin antagonists could block melanoma tumor formation in CB.17 immunodeficient mice, mice were monitored for 8 weeks following subcutaneous injection, and tumor measurements taken at 4- and 8-week time points (Table I). It was determined that YUSAC-2 cells consistently form localized tumors in 6 to 8-week-old female CB.17 SCID/beige mice (Taconic Farms, Germantown, N.Y.) approximately 3-4 weeks following subcutaneous injection of $1-3 \times 10^6$ cells. Animals were monitored for up to 4 months, and neither mortality nor gross metastasis is associated with increasing tumor size (up to 5000 mm³) or ulceration. One day prior to injection, mice were shaved on the right flank, and the regular drinking water was replaced with 5% sucrose alone or containing 100 mg/ml tet as described (Shockett et al., 1995). Cells were harvested in log-phase growth, washed twice in PBS, resuspended in PBS ($12 \times 10^6$ cells per ml) and injected (0.25 ml, $3 \times 10^6$ cells) subcutaneously. The drinking water was changed every 2-3 days. Tumor size was determined by the product of two perpendicular diameters and the height above the skin surface.

Untransfected YUSAC-2 cells readily formed localized nodular amelanotic tumors, and tumor formation was not affected by the addition or absence of tet from the drinking water (FIG. 8D). Histologic analysis revealed sheets of large epitheloid malignant cells that stained positively for HMB-45, a marker of human melanoma cells (not shown; Kikuchi et al., 1996). The HMB-45 antibody (Zymed Laboratories, San Francisco, Calif.) was used according to the manufacturer's instructions. By contrast, F5.C4 cells transfected with survivin $Thr^{34} \rightarrow Ala$ did not form tumors in 13 of 15 (87%) animals when tet was withheld from the drinking water (FIG. 8D, Table I). These animals remained tumor-free for an additional 3-month observation period. Tumors that formed in two tet-deprived animals were considerably smaller in size and appeared with a markedly delayed onset compared to those in animals given tet (Table I). Similar results were obtained in animals injected with subclones F5.E5 and B8, transfected with survivin $Thr^{34} \rightarrow Ala$ and survivin antisense, respectively (Table I).

Table 1. Summary of tumor formation for all animals. CB.17 mice were injected with cells and tet was added or withheld from the drinking water. In this "tet– off" promoter system, the transgene is expressed only in the absence of tet. Tumor incidence is reported for animals observed at 4 and 8 weeks as indicated. Mean tumor size (mm³)±standard deviation is noted only for mice that had formed tumors at the indicated observation points. The slightly smaller size of tumors formed by survivin antagonist subclones compared to untransfected YUSAC-2 cells may be due to some leakiness of the promoter system or an unexplained consequence of transgene insertion.

| Cell line | Transgene | Tet | 4 Weeks | | 8 Weeks | |
|---|---|---|---|---|---|---|
| | | | Tumors formed | Tumor size | Tumors formed | Tumor size |
| YUSAC-2 | None | present | 5/5 (100%) | 295 ± 129 | 5/5 (100%) | 2580 ± 1426 |
| YUSAC-2 | None | absent | 5/5 (100%) | 358 ± 283 | 5/5 (100%) | 2086 ± 1228 |
| F5.C4 | Survivin $Thr^{34} \rightarrow Ala$ | present | 3/4 (75%) | 181 ± 18 | 4/4 (100%) | 1533 ± 1019 |
| F5.C4 | Survivin $Thr^{34} \rightarrow Ala$ | absent | 0/15 (0%) | — | 2/15 (13%) | 278 ± 116 |
| F5.E5 | Survivin $Thr^{34} \rightarrow Ala$ | present | 3/4 (75%) | 132 ± 115 | 3/4 (75%) | 924 ± 710 |
| F5.E5 | Survivin $Thr^{34} \rightarrow Ala$ | absent | 0/5 (100%) | — | 0/5 (100%) | — |
| B8 | Survivin antisense | present | 5/5 (100%) | 153 ± 98 | 5/5 (100%) | 1249 ± 559 |
| B8 | Survivin antisense | absent | 0/5 (100%) | — | 2/5 (40%) | 164 ± 23 |

Example 8

The Effect of Survivin Antagonists on Established Tumors

Next, the effect of survivin $Thr^{34} \rightarrow Ala$ on established tumors was assessed. Fifteen mice were injected with F5.C4 cells and tet was provided to permit tumor formation. Once tumors became apparent (20-50 mm³), tet was withheld from the drinking water and tumors were monitored for 5 weeks.

None of the tumors grew at a rate comparable to F5.C4 tumors in animals maintained on tet (FIG. 10A). Rather, a spectrum of growth curves with some tumors failing to grow at all after tet was withdrawn was observed (FIG. 10A). Histologic analysis revealed that induction of survivin Thr$^{34}$→Ala was associated with massive areas of necrosis and prominent cellular apoptosis by TUNEL, suggesting that changes in tumor mass in these animals did not reflect actual tumor growth. Withdrawal of tet from F5.C4 tumors was also associated with lack of normal mitotic figures and the presence of aberrant mitoses, consistent with the dysregulation of mitotic progression associated with survivin targeting in vitro (Li et al., 1998). In the two small F5.C4 tumors that formed in the absence of tet (Table I), a similar pattern of apoptotic cell death was seen (not shown).

Next, it was determined whether these effects on tumor growth and viability observed in vivo could be attributed to spontaneous apoptosis induced by tet-regulated expression of survivin Thr$^{34}$→Ala. Cell lines were re-established from several of these tumors and assessed for tet-regulated induction of apoptosis in vitro. Tumors were surgically excised and skin and subcutaneous tissues were dissected away. Tumors were then cut into small pieces with a razor blade and dissociated into a single-cell suspension by vigorous vortexing in PBS. Cells were washed twice in PBS, resuspended in selection medium containing G418 and tet, and cultured for 2-3 passages. These cells retained tet-responsiveness as removal of tet from the culture medium was associated with generation of hypodiploid (apoptotic) cells by DNA content analysis (FIG. 10B). The persistence of some viable cells in tet-deprived tumors may reflect an inability to remove tet completely from the animal and achieve maximal transgene expression in vivo. In addition, inhibition of survivin may not eliminate non-dividing cells given its selective action during the G2/M phase of the cell cycle (Li et al., 1999).

Although the present invention has been described in detail with reference to examples above, it is understood that various modifications can be made without departing from the spirit of the invention. Accordingly, the invention is limited only by the following claims.

ADDITIONAL REFERENCES

The following articles are hereby incorporated by reference in their entirety:

Adida, C., Crotty, P. L., McGrath, J., Berrebi, D., Diebold, J. and Altieri, D. C. (1998) Developmentally regulated expression of the novel cancer anti-apoptosis gene Survivin in human and mouse differentiation. Am. J. Pathol. 152:43-49.

Ambrosini, G., Adida, C., and Altieri, D. C. (1997). A novel anti-apoptosis gene, survivin, expressed in cancer and lymphoma. Nat. Med. 3, 917-921.

Blangy, A., Arnaud, L., and Nigg, E. A. (1997). Phosphorylation by p34 cdc2 protein kinase regulates binding of the kinesin-related motor HsEg5 to the dynactin subunit p150 Glued. J. Biol. Chem. 272, 19418-19424.

Boldin, M. P., Goncharov, T. M., Goltsev, Y. V., and Wallach, D. (1996). Involvement of MACH, a novel Mort1/FADD-interacting protease, in Fas/APO-1 and TNF receptor-induced cell death. Cell 85, 803-815.

Bossy-Wetzel, E., and Green, D. R. (1999). Caspases induce cytochrome c release from mitochondria by activating cytosolic factors. J. Biol. Chem. 274, 17484-17490.

Chan, T. A., Hermeking, H., Lengauer, C., Kinzler, K. W., and Vogelstein, B. (1999). 14-3-3 is required to prevent mitotic catastrophe after DNA damage. Nature 401, 616-620.

Deveraux, Q. L., Leo, E., Stennicke, H. R., Welsh, K., Salvesen, G. S., and Reed, J. C. (1999). Cleavage of human inhibitor of apoptosis protein XIAP results in fragments with distinct specificities for caspases. EMBO J. 18, 5242-5251.

Deveraux, Q. L., and Reed, J. C. (1999). IAP family proteins-suppressors of apoptosis. Genes Dev. 13, 239-252.

Duan, H., Orth, K., Chinnaiyan, A. M., Poirier, G. G., Froelich, C. J., He, W.-W., and Dixit, V. M. (1996). ICE-LAP6, a novel member of the ICE-Ced3 gene family, is activated by the cytotoxic T cell protease granzyme B. J. Biol. Chem. 271, 16720-16724.

Evan, G., and Littlewood, T. (1998). A matter of life and cell death. Science 281, 1317-1322.

Fearnhead, H. O., Rodriguez, J., Govek, E. E., Guo, W., Kobayashi, R., Hannon, G., and Lazebnik, Y. A. (1998). Oncogene-dependent apoptosis is mediated by caspase-9. Proc. Natl. Acad. Sci. U.S.A. 95, 13664-13669.

Field, C., Li, R., and Oegema, K. (1999). Cytokinesis in eukaryotes: a mechanistic comparison. Curr. Op. Cell Biol. 11, 68-80.

Fraser, A. G., James, C., Evan, G. I., and Hengartner, M. O. (1999). *Caenorhabditis elegans* inhibitor of apoptosis protein (IAP) homologue BIR-1 plays a conserved role in cytokinesis. Curr. Biol. 9, 292-301.

Green, D. R. (1998). Apoptotic pathways: The roads to ruin. Cell 94, 695-698.

Grossman, D., McNiff, J. M., Li, F., and Altieri, D.C. (1999a). Lab Invest 79, 1121.

Grossman, D., McNiff, J. M., Li, F., and Altieri, D.C. (1999b). Expression and targeting of the apoptosis inhibitor, survivin, in human melanoma. J. Invest. Dermatol. 113, 1076-81.

Hajduch, M., Havlieek, L., Vesely, J., Novotny, R., Mihal, V., and Strnad, M. (1999). Synthetic cyclin dependent kinase inhibitors. New generation of potent anti-cancer drugs. Adv. Exp. Med. Biol. 457, 341-353.

Haldar, S., Basu, A., and Croce, C. M. (1997). Bcl2 is the guardian of microtubule integrity. Cancer Res. 57, 229-233.

Harrington, E. A., Bennett, M. R., Fanidi, A., and Evan, G. I. (1994). c-Myc-induced apoptosis in fibroblasts is inhibited by specific cytokines. EMBO J. 13, 3286-3295.

Holmes, J. K., and Solomon, M. J. (1996). A predictive scale for evaluating cyclin-dependent kinase substrates. A comparison of p34 cdc2 and p33 cdk2. J. Biol. Chem. 271, 25240-25246.

Hu, Y., Benedict, M. A., Ding, L., and Nunez, G. (1999). Role of cytochrome c and dATP/ATP hydrolysis in Apaf-1-mediated caspase-9 activation and apoptosis. EMBO J. 18, 3586-3595.

Huang, D. C. S., O'Reilly, L. A., Strasser, A., and Cory, S. (1997). The anti-apoptosis function of bcl-2 can be genetically separated from its inhibitory effect on cell cycle entry. EMBO J. 16, 4628-4638.

Hunter, T. (1997). Oncoprotein networks. Cell 88, 333-346.

Ito, T., Deng, X., Carr, B., and May, W. S. (1997). Bcl-2 phosphorylation required for anti-apoptosis function. J. Biol. Chem. 272, 11671-11673.

Jansen et al., (1998) Nat. Med. 4, 232.

Krajewski, S., Krajewska, M., Ellerby, L. M., Welsh, K., Xie, Z., Deveraux, Q. L., Salvesen, G. S., Bredesen, D. E., Rosenthal, R. E., Fiskum, G., and Reed, J. C. (1999). Release of caspase-9 from mitochondria during neuronal apoptosis and cerebral ischemia. Proc. Natl. Acad. Sci. U.S.A. 96, 5752-7.

Kikuchi, A., Shimizu, H., and Nishikawa, T., (1996) Br J Dermatol 135, 400.

Levine, A. J. (1997). p53, the cellular gatekeeper for growth and division. Cell 88, 323-331.

Li, F., Ackermann, E. J., Bennett, C. F., Rothermel, A. L., Plescia, J., Tognin, S., Villa, A., Marchisio, P. C., and Altieri, D.C. (1999). Pleiotropic cell-division defects and apoptosis induced by interference with survivin function. Nat. Cell Biolog. 1, 461-466.

Li, F., Ambrosini, G., Chu, E. Y., Plescia, J., Tognin, S., Marchisio, P. C., and Altieri, D. C. (1998). Control of apoptosis and mitotic spindle checkpoint by survivin. Nature 396, 580-584.

Linette, G. P., Li, Y., Roth, K., and Korsmeyer, S. J. (1996). Cross talk between cell death and cell cycle progression: BCL-2 regulates NFAT-mediated activation. Proc. Natl. Acad. Sci. U.S.A. 93, 9545-9552.

Ling, Y.-H., Tornos, C., and Perez-Soler, R. (1998). Phosphorylation of Bcl-2 is a marker of M phase events and not a determinant of apoptosis. J. Biol. Chem. 273, 18984-18991.

Lowe, M., Rabouille, C., Nakamura, N., Watson, R., Jackman, M., Jamsa, E., Rahman, D., Pappin, D. J. C., and Warren, G. (1998). Cdc2 kinase directly phosphorylates the cis-Golgi matrix protein GM130 and is required for Golgi fragmentation in mitosis. Cell 94, 783-793.

Martin, S. J., McGahon, A. J., Nishioka, W. K., La Face, D., Guo, X., Th'Ng, J., Bradbury, E. M., and Green, D. R. (1995). p34 cdc2 and apoptosis. Science 269, 106-107.

Merdes, A., and Cleveland, D. W. (1997). Pathways of spindle formation: Different mechanisms; conserved components. J. Cell Biol. 138, 953-956.

Minn, A. J., Boise, L. H., and Thompson, C. B. (1996). Expression of Bcl-X L and loss of p53 can cooperate to overcome a cell cycle checkpoint induced by mitotic spindle damage. Genes Dev. 10, 2621-2631.

Milligan et al., (1993). J. Med. Chem. 36, 1923.

Nicklas, R. B. (1997). How cells get the right chromosome. Science 275, 632-637.

Nigg, E. A. (1993). Cellular substrates of p34cdc2 and its companion cyclin-dependent kinases. Trends Cell Biol. 3, 296-301.

Nurse, P. (1994). Ordering S phase and M phase in the cell cycle. Cell 79, 547-550.

Ookata, K., Hisanaga, S., Sugita, M., Okuyama, A., Murofishi, H., Kitazawa, H., Chari, S., Bulinski, J. C., and Kishimoto, T. (1997). MAP4 is the in vivo substrate for CDC2 kinase in HeLa cells: identification of an M-phase specific and a cell cycle-independent phosphorylation site in MAP4. Biochemistry 36, 15873-83.

Pan, G., O'Rourke, K., and Dixit, V. M. (1998). Caspase-9, Bcl-X L, and Apaf-1 form a ternary complex. J. Biol. Chem. 273, 5841-5845.

Patel, V., Senderowicz, A. M., Pinto, D., Jr., Igishi, T., Raffeld, M., Quintanilla-Martinez, L., Ensley, J. F., Sausville, E. A., and Gutkind, J. S. (1998). Flavopiridol, a novel cyclin-dependent kinase inhibitor, suppresses the growth of head and neck squamous cell carcinomas by inducing apoptosis. J. Clin. Invest. 102, 1674-1681.

Paulowich, A. G., Toczyski, D. P., and Hartwell, L. H. (1997). When checkpoints fail. Cell 88, 315-321.

Pines, J. (1999). Four-dimensional control of the cell cycle. Nat. Cell Biolog. 1, E73-E79.

Porter, A. G. (1999). Protein translocation in apoptosis. Trends Cell Biol. 9, 394-401.

Rodriguez, J., and Lazebnik, Y. (1999). Caspase-9 and APAF-1 form an active holoenzyme. Genes Dev. 13, 3179-3184.

Roy, N., Mahadevan, M. S., McLean, M., Shutler, G., Yaraghi, Z., Farahani, R., Baird, S., Besner-Johnston, A., Lefebvre, C., Kang, X., Salith, M., Aubry, H., Tamai, K., Guan, X., Ioannou, P., Crawford, T. O., de Jong, P. J., Surh, L., Ikeda, J.-E., Korneluk, R. G. and MacKenzie, A. (1995) The gene for neuronal apoptosis inhibitory protein is partially deleted in individuals with spinal muscular atrophy. Cell 80:167-178.

Salvesen, G. S., and Dixit, V. M. (1997). Caspases: intracellular signaling by proteolysis. Cell 91, 443-446.

Scatena, C. D., Stewart, Z. A., Mays, D., Tang, L. J., Keefer, C. J., Leach, S. D., and Pietenpol, J. A. (1998). Mitotic phosphorylation of Bcl-2 during normal cell cycle progression and taxol-induced growth arrest. J. Biol. Chem. 273, 30777-30784.

Shi, L., Nishioka, W. K., Thng, J., Bradbury, E. M., Litchfield, D. W., and Greenberg, E. H. (1994). Premature p34 cdc2 activation required for apoptosis. Science 263, 1143-1145.

Shockett, P., Difilippantonio, M., Hellman, N., and Schatz, D. G. (1995). A modified tetracycline-regulated system provides autoregulatory, inducible gene expression in cultured cells and transgenic mice. Proc. Natl. Acad. Sci. U.S.A. 92, 6522-6526.

Shuster, C. B., and Burgess, D. R. (1999). Parameters that specify the timing of cytokinesis. J. Cell Biol. 146, 981-92.

Soengas, M. S., Alarcon, R. M., Yoshida, H., Giaccia, A. J., Hakem, R., Mak, T. W., and Lowe, S. W. (1999). Apaf-1 and caspase-9 in p53-dependent apoptosis and tumor inhibition. Science 284, 156-159.

Stennicke, H. R., Deveraux, W. L., Humke, E. W., Reed, J. C., Dixit, V. M., and Salvesen, G. S. (1999). Caspase-9 can be activated without proteolytic processing. J. Biol. Chem. 274, 8359-8362.

Sun, C., Cai, M., Gunasekera, A. H., Meadows, R. P., Wang, H., Chen, J., Zhang, H., Wu, W., Xu, N., Ng, S. C., and Fesik, S. W. (1999). NMR structure and mutagenesis of the inhibitor-of-apoptosis protein XIAP. Nature 401, 818-822.

Terada, Y., Tatsuka, M., Suzuki, F., Yasuda, Y., Fujita, S., and Otsu, M. (1998). AIM-1: a mammalian midbody-associated protein required for cytokinesis. EMBO J. 17, 667-676. Thomberry, N. A., and Lazebnik, Y. (1998). Caspases: enemies within. Science 281, 1312-1316.

Uhlmann et al., (1990). Chemical Reviews 90, 543.

Uren, A. G., Beilharz, T., O'Connell, M. J., Bugg, S. J., van Driel, R., Vaux, D. L., and Lithgow, T. (1999). Role for yeast inhibitor of apoptosis (IAP)-like proteins in cell division. Proc. Natl. Acad. Sci. U.S.A. 96, 10170-10175.

Vaux, D. L., and Korsmeyer, S. J. (1999). Cell death in development. Cell 96, 245-254.

Velculescu, V. E., Madden, S. L., Zhang, L., Lash, A. E., Yu, J., Rago, C., Lal, A., Wang, C. J., Beaudry, G. A., Ciriello, K. M., Cook, B. P., Dufault, M. R., Ferguson, A. T., Gao, Y., He, T. C., Hermeking, H., Hiraldo, S. K., Hwang, P. M., Lopez, M. A., Luderer, H. F., Mathews, B., Petroziello, J. M., Polyak, K., Zawel, L., Zhang, W., Zhang, X., Zhou, W., Haluska, F. G., Jen, J., Sukumar, S., Landes, G. M., Riggins, G. J., Vogelstein, B., and Kinzler, K. W. (1999). Analysis of human transcriptomes. Nat. Genet. 23, 387-388.

Waldman, T., Lengauer, C., Kinzler, K. W., and Vogelstein, B. (1996). Uncoupling of S phase and mitosis induced by anticancer agents in cells lacking p21. Nature 381, 713-716.

Yamamoto, K., Ichijo, H., and Korsmeyer, S. J. (1999). Bcl-2 is phosphorylated and inactivated by an ASK1/Jun N-terminal protein kinase pathway normally activated at G(2)/M. Mol. Cell. Biol. 19, 8469-8478.

Yoon, H.-J., and Carbon, J. (1999). Participation of Bir1p, a member of the inhibitor of apoptosis family, in yeast chromosome segregation events. Proc. Natl. Acad. Sci. U.S.A. 96, 13208-13213.

Zou, H., Li, Y., Liu, X., and Wang, X. (1999). An APAF-1-cytochrome c multimeric complex is a functional apoptosome that activates procaspase-9. J. Biol. Chem. 274, 11549-11556.

---

The invention claimed is:

1. A method of inhibiting the growth of a tumor cell comprising administering an effective amount of a nucleic acid encoding survivin $Thr^{34} \rightarrow Ala$ to the tumor cell.

2. The method of claim 1, wherein the tumor cell is in a tumor mass.

3. The method of claim 2, wherein the tumor mass is present in a mammal.

4. The method of claim 3, wherein the tumor mass is a melanoma.

5. The method of claim 1, wherein the method inhibits the growth of a tumor cell in vitro.

6. The method of claim 2, wherein the method inhibits the growth of a tumor mass in vivo.

7. The method of claim 1, wherein the method inhibits the growth of a tumor cell is in vivo.

* * * * *

SEQUENCE LISTING

<160> NUMBER OF SEQ ID NOS: 21

<210> SEQ ID NO 1
<211> LENGTH: 17
<212> TYPE: PRT
<213> ORGANISM: Homo sapiens
<220> FEATURE:
<221> NAME/KEY: MOD_RES
<222> LOCATION: (7)
<223> OTHER INFORMATION: PHOSPHORYLATION

<400> SEQUENCE: 1

Leu Glu Gly Cys Ala Cys Thr Pro Glu Arg Met Ala Glu Ala Gly Phe
 1               5                  10                  15

Ile

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide for mutagenesis

<400> SEQUENCE: 2
ggctgcgcct gcgccccgga gcggatg                                      27

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence:  Forward PCR
      primer

<400> SEQUENCE: 3
cccaagctta tgtatccgta tgatgttcct gattatgctg gtgccccgac gttgccc     57

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:  Reverse PCR
      primer

<400> SEQUENCE: 4
cgggatccgg aagtggtgca gccactctg                                    29

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:  Reverse PCR
      primer

<400> SEQUENCE: 5
acgaattcaa tccatggcag ccag                                         24

```
<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Forward PCR
      primer

<400> SEQUENCE: 6
cccaagcttc catggacgaa gcggatcgg                                              29

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Reverse PCR
      primer

<400> SEQUENCE: 7
cggaattctt agtccagctg gtcgaaggtc                                             30

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Reverse PCR
      primer

<400> SEQUENCE: 8
gtctttctgc tccccaccgg cggcctggat gaaaaagagc                                  40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Forward PCR
      primer

<400> SEQUENCE: 9
gctctttttc atccaggccg ccggtgggga gcagaaagac                                  40

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Reverse PCR
      primer

<400> SEQUENCE: 10
cggaattctt atgatgtttt aaagaaaagt tttttcc                                     37

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: p34-cdc2
      consensus site for phosphorylation
<220> FEATURE:
<221> NAME/KEY: VARIANT
<222> LOCATION: (1)..(4)
<223> OTHER INFORMATION: X at position 1 = Ser or Thr; X at position 3 =
      any amino acid; X at position 4 = Lys or Arg.
```

-continued

```
<400> SEQUENCE: 11

Xaa Pro Xaa Xaa
  1

<210> SEQ ID NO 12
<211> LENGTH: 9
<212> TYPE: PRT
<213> ORGANISM: Homo sapiens
<220> FEATURE:
<223> OTHER INFORMATION: Survivin phosphorylation motif

<400> SEQUENCE: 12

Cys Ala Cys Thr Pro Glu Arg Met Ala
  1               5

<210> SEQ ID NO 13
<211> LENGTH: 9
<212> TYPE: PRT
<213> ORGANISM: Mus musculus
<220> FEATURE:
<223> OTHER INFORMATION: Survivin phosphorylation motif

<400> SEQUENCE: 13

Cys Ala Cys Thr Pro Glu Arg Met Ala
  1               5

<210> SEQ ID NO 14
<211> LENGTH: 9
<212> TYPE: PRT
<213> ORGANISM: Homo sapiens
<220> FEATURE:
<223> OTHER INFORMATION: BRUCE phosphorylation motif

<400> SEQUENCE: 14

Arg Trp Ala Gln Pro Asp Pro Met Ala
  1               5

<210> SEQ ID NO 15
<211> LENGTH: 7
<212> TYPE: PRT
<213> ORGANISM: Homo sapiens
<220> FEATURE:
<223> OTHER INFORMATION: NAIP phosphorylation motif

<400> SEQUENCE: 15

Trp Ile Pro Gln Glu Met Ala
  1               5

<210> SEQ ID NO 16
<211> LENGTH: 8
<212> TYPE: PRT
<213> ORGANISM: Homo sapiens
<220> FEATURE:
<223> OTHER INFORMATION: XIAP phosphorylation site

<400> SEQUENCE: 16

Pro Val Ser Ala Ser Thr Leu Ala
  1               5

<210> SEQ ID NO 17
<211> LENGTH: 9
<212> TYPE: PRT
<213> ORGANISM: Caenorhabditis elegans
<220> FEATURE:
<223> OTHER INFORMATION: BIR1 phosphorylation motif

<400> SEQUENCE: 17
```

```
Ala Lys Cys Ser Gln Ala Val Ala Ala
  1               5

<210> SEQ ID NO 18
<211> LENGTH: 9
<212> TYPE: PRT
<213> ORGANISM: Schizosaccharomyces pombe
<220> FEATURE:
<223> OTHER INFORMATION: BIRP phosphorylation motif

<400> SEQUENCE: 18

Ala Lys Pro Thr Pro Glu Thr Leu Ala
  1               5

<210> SEQ ID NO 19
<211> LENGTH: 9
<212> TYPE: PRT
<213> ORGANISM: Saccharomyces cerevisiae
<220> FEATURE:
<223> OTHER INFORMATION: BIR-1 phosphorylation motif

<400> SEQUENCE: 19

Lys Val Ile Pro Tyr Gln Ala Met Ala
  1               5

<210> SEQ ID NO 20
<211> LENGTH: 9
<212> TYPE: PRT
<213> ORGANISM: Baculovirus
<220> FEATURE:
<223> OTHER INFORMATION: OpIAP phosphorylation motif

<400> SEQUENCE: 20

Phe Gln Leu Glu Pro Ser Arg Met Ala
  1               5

<210> SEQ ID NO 21
<211> LENGTH: 9
<212> TYPE: PRT
<213> ORGANISM: Drosophila melanogaster
<220> FEATURE:
<223> OTHER INFORMATION: DIAP phosphorylation motif

<400> SEQUENCE: 21

Trp Gln Leu Asp Lys Arg Gln Leu Ala
  1               5
```